(12) United States Patent
Steinman et al.

(10) Patent No.: US 7,659,119 B2
(45) Date of Patent: *Feb. 9, 2010

(54) METHOD AND COMPOSITIONS FOR OBTAINING MATURE DENDRITIC CELLS

(75) Inventors: Ralph M. Steinman, Westport, CT (US); Nina Bhardwaj, Montclair, NJ (US); Gerold Schuler, Spardorf (DE)

(73) Assignees: Argos Therapeutics, Inc., Durham, NC (US); The Rockefeller University, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/600,483

(22) Filed: Feb. 12, 1996

(65) Prior Publication Data

US 2003/0096314 A1    May 22, 2003

(51) Int. Cl.
*C12N 5/02* (2006.01)
(52) U.S. Cl. .................. 435/377; 435/385; 435/386; 436/63; 436/68
(58) Field of Classification Search .................. 435/5, 435/7.2, 7.1, 7.24; 436/63, 68
See application file for complete search history.

(56) References Cited

U.S. PATENT DOCUMENTS

| | | |
|---|---|---|
| 4,861,589 A | 8/1989 | Ju |
| 5,529,903 A | 6/1996 | Kubler et al. |
| 5,851,756 A | 12/1998 | Steinman et al. |
| 5,994,126 A | 11/1999 | Steinman et al. |

FOREIGN PATENT DOCUMENTS

| | | |
|---|---|---|
| EP | 0 546 787 A2 | 6/1993 |
| EP | 0 563 485 A1 | 10/1993 |
| WO | WO 91/13632 | 9/1991 |
| WO | WO 93/20185 | 10/1993 |
| WO | WO 94/02156 | 2/1994 |
| WO | WO 95/15340 | 6/1995 |
| WO | WO 95/28479 | 10/1995 |
| WO | WO 95/34638 | 12/1995 |

OTHER PUBLICATIONS

O'Doheryt, et al.: Dendritic cells freshly isolated from human blood . . . : J. Exp. Med. : vol. 178: pp. 1067-1078, Sep. 1993.*
Sallusto, et al.: Efficient presentation of soluble antigen . . . : J. Exp. Med.: vol. 179: pp. 1109-1118, Apr. 1994.*
Romani, et al.: Proliferation dendritic cell progenitors in human blood: J. Exp. Med.: vol. 180: pp. 83-93, Jul. 1994.*
Bernhard, H., et al. Cancer Res. Mar. 1, 1995;55(5):1099-1104.*
Peripheral Stem Cells Made to Work—*The Lancet*, Mar. 14, 1992, vol. 339, pp. 648-649.
Abbas, et al. "Uptake & Processing of Extracellular Protein Antigens by Antigen-Presenting Cells", W.B. Saunders Co. 1991 at 124-126.
Abbas, et al. *Cellular and Molecular Immunology*, W.B. Saunders Co. Philadelphia 1991 at 117.
Abbas, et al. *Cellular and Molecular Immunology*, Second Edition, Section IV, pp. 328-329.
Agger, R., et al. "Two Populations of Splenic Dendritic Cells Detected With M342, a New Monoclonal to an Intracellular Antigen of Interdigitating Dendritic Cells and Some B Lymphocytes", *J. Leukocyte Biol.* 52:34-42, Jul. 1992.
Akagawa, et al. "IL-4 Stimulates the Generation of Dendritic Cells and Multinucleated Giant Cells From Human Monocytes", *Lymphokine and Cytokine Research*, vol. 12, No. 5, Oct. 1993, p. 326.
Alijagic, et al. "Dendritic Cells Generated From Peripheral Blood Transfected With Human Tyrosinase Induce Specific T Cell Activation." *Eur. J. Immunology*. vol. 25, pp. 3100-3107, 1995.
Ardavin, et al. "Thymic Dendritic Cells and T Cells Develop Simultaneously in the Thymus From a Common Precursor Population", *Nature* 362:761-763, Apr. 1993.
Austyn, J.M., "Lymphoid Dendritic Cells" *Immunology*, vol. 62, pp. 161-170, 1987.
Austyn, et al. "Isolation and Characterization of Dendritic Cells From Mouse Heart and Kidney." *J. Immunology*, vol. 152, pp. 2401-2410, 1994.
Baker, et al. *Basic and Clinical Immunology*, Seventh Ed., Appelton & Lange, Norwalk, CT, 1991.
Bakker, et al. "Generation of Antimelanoma Cytotoxic T Lymphocytes From Healthy Donors After Presentation of Melanoma-Associated Antigen-Derived Eptiopes by Dendritic Cells in Vitro." *Cancer Research*, vol. 55, pp. 5330-5334, Nov. 15, 1995.
Barfoot, et al. "Some Properties of Dendritic Macrophages From Peripheral Lymph", *Immunology* 1989, vol. 68, No. 2. pp. 233-239.
Bender, et al. "Improved Methods for the Generation of Dendritic Cells From Nonproliferating Progenitors in Human Blood", *J. Immunol.*, vol. 196, 1996, pp. 121-135.
Bender, et al. "Inactivated Influenza Virus, When Presented on Dendritic Cells, Elicit Human $CD8^=$ Cytolytic T Cell Responses." *J. Exp. Med.*, vol. 182, pp. 1663-1671, Dec. 1995.

(Continued)

*Primary Examiner*—G. R Ewoldt
(74) *Attorney, Agent, or Firm*—Elaine T. Sale; Leigh W. Thorne

(57) ABSTRACT

We describe an improved method for generating sizable numbers of mature dendritic cells from nonproliferating progenitors in human blood. The first step or "priming" phase is a culture of T cell depleted mononuclear cells in medium supplemented with GM-CSF and IL-4 to produce immature dendritic cells. The second step or "differentiation" phase requires the exposure to dendritic cell maturation factor such as monocyte conditioned medium. Using this two-step approach, substantial yields are obtained. The dendritic cells derive from this method have all the features of mature cells. They include a stellate cell shape, nonadherence to plastic, and very strong T cell stimulatory activity. The mature dendritic cells produced according to this invention are useful for activating T cells.

10 Claims, 17 Drawing Sheets

OTHER PUBLICATIONS

Bhardwaj, et al. "Influenza Virus-Infected Dendritic Cells Stimulate Strong Proliferative and Cytolytic Responses From Human CD8⁻ T Cells." *J. Clin. Invest.* vol. 94, pp. 797-807, Aug. 1994.

Bhardwaj, et al. "IL-12 in Conjunction With Dendritic Cells Enhances Anti-Viral, CD8= CTL Responses in Vitro." *J. Clin Invest.*, vol. 98, No. 3, pp. 715-722, Aug. 1996.

Boog, et al. "Abolition of Specific Immune Response Defect by Immunization With Dendritic Cells", *Nature*, Nov. 7, 1985, vol. 318, pp. 59-62.

Boon "Tumor Antigens Recognized by T Lymphocytes", *Annual Review of Immunology*, vol. 12, pp. 337-365, 1994.

Boon, et al. "Tumor Antigens Recognized by Cytolytic T Lymphocytes: Present Perspectives for Specific Immunotherapy", *Int. J. Cancer*, vol. 54, pp. 177-180 (1993).

Bowers, et al. "Differentiation of Dendritic Cells in Cultures of Rat Bone Marrow Cells", *J. Exp. Med.*, Apr. 1986, vol. 163, pp. 872-883.

Britz, et al. "Specialized Antigen-Presenting Cells, Splenic Dendritic Cells and Peritoneal-Exudate Cells Induced by Mycobacteria Activate Effector T Cells That are Resistant to Suppression", *J. Exp. Med.*, May 1982, vol. 155, pp. 1344-1356.

Bujdoso, et al. "Characterization of Sheep Afferent Lymph Dendritic Cells and Their Role in Antigen Carriage", *J. Exp. Med.*, Oct. 1989, vol. 170, pp. 1285-1302.

Caux, et al. "Recent Advances in the Study of Dendritic Cells and Follicular Dendritic Cells." *Immunology Today*, vol. 16, No. 1, pp. 2-4, 1995.

Caux, et al. "Human Dendritic Langerhans Cells Generated in Vitro From CD34+ Progenitors Can Prime Naive CD4+ T Cells and Process Soluble Antigen." *J. Immunology.* vol. 155, pp. 5427-5435, 1995.

Caux, et al. "CD34+ Hematopoietic Progenitors From Human Cord Blood Differentiate Along Two Independent Dendritic Cell Pathways in Response to GM-CSF+ TNFα." *J. Exp. Med.* vol. 184, pp. 695-706, Aug. 1996.

Caux, et al. "GM and TNF-α Cooperate in the Generation of Dendritic Langerhans Cells", *Nature*, vol. 360, Nov. 19, 1992, pp. 258-261.

Caux, et al. "Tumor Necrosis Factor-Alpha Strongly Potentiates Interleukin-3 and Granulocyte-Macrophage Colony-Stimulating Factor-Induced Proliferation of Human CD34+ Hematopoietic Progenitor Cells", *Blood*, Jun. 15, 1990, vol. 75, No. 12, pp. 2292-2298.

Chatterjee, et al. "Idiotypic Antibody Immunotherapy of Cancer", *Cancer Immunology Immunotherapy*, vol. 38, pp. 75-82 (1994).

Cohen, et al. "Murine Epidermal Langerhans Cells and Splenic Dendritic Cells Present Tumor-Associated Antigens to Primed T Cells", *Eur. J. Immunol.*, vol. 24, pp. 315-319, (1994).

Coulie, et al. "Genes Coding for Antigens Recognized on Human Tumors by Autologous Cytolytic T Lymphocytes", *Ann. NY Acad. Sci.*, vol. 690, Aug. 12, 1993, pp. 113-119.

Crowley, et al. "Dendritic Cells are the Principal Cells in Mouse Spleen Bearing Immunogenic Fragments of Foreign Proteins", *J. Exp. Med.*, vol. 172, No. 1, Jul. 1, 1990, pp. 383-386.

De Bruijn, et al. "Mechanisms of Induction of Primary Virus-Specific Cytotoxic T Lymphocyte Responses", *Eur. J. Immunol.*, vol. 22, 1992, pp. 3013-3020.

Dechema Biotechnol. Conf. 4 (Pt. A Lect. Dechema Annu. Meet. Biotech. 8th, 1990), pp. 181-184.

Dedhar, et al. "Human Granulocyte-Macrophage Colony-Stimulating Factor is a Growth Factor Active on a Variety of Cell Types of Nonhemopoietic Origin", *Prac. Natl. Acad. Sci, USA*, vol. 85, Dec. 1988, pp. 9253-9257.

Disis, et al. "In Vitro Generation of Human Cytolytic T-Cells Specific for Peptides Derived From the HER-2/neu Protoncogene Protein", *Cancer Research*, vol. 54, Feb. 15, 1994, pp. 1071-1076.

Dranoff, et al. "Vaccination With Irradiated Tumor Cells Engineered to Secrete Murine Granulocyte-Macrophage Colony-Stimulating Factor Stimulates Potent, Specific, and Long-Lasting Anti-Tumor Immunity", *Prac. Natl. Acad. Sci., USA*, vol. 90, No. 8, Apr. 1993, pp. 3539-3543.

Eaves "Peripheral Blood Stem Cells Reach New Heights", *Blood*, vol. 82, No. 7. Oct. 1, 1993, pp. 1957-1959.

Edgington "How Sweet it is: Selectin-Mediating Drugs", *Biotechnology*, vol. 10, Apr. 1992, pp. 383-389.

Egner, et al. "The Phenotype of Freshly Isolated and Cultured Human Bone Marrow Allositmulatory Cells: Possible Heterogeneity in Bone Marrow Dendritic Cell Populations." *Immunology* vol. 85, pp. 611-615.

Ema, et al. "Colony Formation of Clone-Sorted Human Hematopoietic Progenitors", *Blood*, vol. 75, No. 10, May 15, 1990, pp. 1941-1946.

Faustman, et al. "Prevention of Rejection of Murine Islet Allografts by Pretreatment With Anti-Dendritic Cell Antibody", *Prac. Natl. Acad. Sci. USA*, vol. 81, Jun. 1984, pp. 3864-3868.

Fisher, et al. "Neoplastic Cells Obtained From Hodgkin's Disease Function as Accessory Cells for Mitogen-Induced Human T Cell Proliferative Responses", *J. Immunol.*, vol. 132, No. 5, May 1984, pp. 2672-2677.

Flamand, et al. "Murine Dendritic Cells Pulsed in Vitro With Tumor Antigen Induce Tumor Resistance in Vivo", *Eur. J. Immunol.* vol. 24, 1994, pp. 605-610.

Flamand, et al. "Vaccination With Tumor Antigen-Pulsed Dendritic Cells Induces in Vivo Resistance to a B Cell Lymphoma", *Adv. Exp. Med. Biol.*, vol. 329, 1993, pp. 611-615.

Fossum, S. "Lymph-Borne Dendritic Leucocytes do not Recirculate, but Enter the Lymph Node Paracortex to Become Interdigitating Cells." *Scand. J. Immunol.*, vol. 27, pp. 97-104, (1988).

Francotte, et al. "Enhancement of Antibody Response by Mouse Dendritic Cells Pulsed With Tobacco Mosaic Virus or With Rabbit Antidiotypic Antibodies Raised Against a Private Rabbit Idiotype", *Prac. Natl. Acad. Sci. USA*, vol. 82, Dec. 1985, pp. 8149-8152.

Freudenthal, et al. "The Distinct Surface of Human Blood Dendritic Cells, as Observed After an Improved Isolation Method", *Proc. Natl. Acad. Sci. USA*, vol. 87, Oct. 1990, pp. 7698-7702.

Gaugler, et al. "Human Gene Image-3 Codes for an Antigen Recognized on a Melanoma by Autologous Cytolytic T Lymphocytes", *J. Exp. Med.*, vol. 179, Mar. 1994, pp. 921-930.

Gaur, et al. "Amelioration of Autoimmune Encephalomyelitis by Myelin Basic Protein Synthetic Peptide-Induced Anergy," *Science*, vol. 258, Nov. 27, 1992, pp. 1491-1494.

Gerdes, et al. "Cell Cycle Analysis of a Cell Proliferation-Associated Human Nuclear Antigen Defined by the Monoclonal Antibody Ki-67[1]", *J. Immunol.*, vol. 133, No. 4, Oct. 1984, pp. 1710-1715.

Grabstein, et al. "Cloning of a T Cell Growth Factor That Interacts With the β Chain of the Interleukin-2 Receptor, Science" 264:965-966, May 13, 1994.

Ham, et al. "Cell Culture", *Methods in Enzymology*, vol. LVIII, pp. 44-93 (1979).

Heufler, et al. "Granulocyte/Macrophage Colony-Stimulating Factor and Interleukin 1 Mediate the Maturation of Murine Epidermal Langerhans Cells Into Potent Immunostimulatory Dendritic Cells", *J. Exp. Med.*, vol. 167, Feb. 1988, pp. 700-705.

Holt, et al. "MHC Class ll Antigen-Bearing Dendritic Cells in Pulmonary Tissues of the Rat", *J. Exp. Med.*, vol. 167, Feb. 1988, pp. 262-274.

Hosaka, et al. Entry of Heat-Inactivated Influenza Virus and Induction of Target Susceptibility to Cytotoxic T Cell-Mediated Lysis, *Virus Res.*, Suppl. 1, p. 56, 1985.

Hsu, et al. "Vaccination of Patients With B-Cell Lymphoma Using Autologous Antigen-Pulsed Dendritic Cells", *Nature Medicine*, vol. 2, No. 1, Jan. 1996, pp. 52-58.

Huang, et al. "Role of Bone Marrow-Derived Cells in Presenting MHC Class 1-Restricted Tumor Antigens", *Science*, vol. 264, May 13, 1994, pp. 961-965.

Inaba, et al. "Granulocytes, Macrophages and Dendritic Cells Arise From a Common Major Histocompatibility Complex Class II-Negative Progenitor in Mouse Bone Marrow", *Proc. Natl. Acad. Sci. USA*, vol. 90, No. 7, Apr. 1, 1993, pp. 3038-3042.

Inaba, et al. "Identification of Proliferating Dendritic Cell Precursors in Mouse Blood", *J. Exp. Med.*, vol. 175, May 1992, pp. 1157-1167.

Inaba, K., et al. "Dendritic Cells are Critical Accessory Cells for Thymus-Dependent Antibody Responses in Mouse and Man," *Proc. Natl. Acad. Sci. USA* 80:6041-6045, 1983.

Inaba, et al. "Dendritic Cells Pulsed With Protein Antigens in Vitro Can Prime Antigen-Specific, MHC-Restricted T Cells in Situ", *J. Exp. Med.*, Aug. 1990, vol. 172, pp. 631-640.

Inaba, et al. "Protein Specific Helper T-Lymphocyte Formation Initiated by Dendritic Cells", *Science*, Aug. 2, 1985, vol. 229, No. 4713, pp. 475-479.

Inaba, et al. "Clustering of Dendritic Cells, Helper T Lymphocytes, and Histocompatible B Cells During Primary Antibody Responses In Vitro", *J. Exp. Med.*, Sep. 1984, vol. 160, No. 3, pp. 858-876.

Inaba, et al. "Properties of Memory T Lymphocytes Isolated From the Mixed Leukocyte Reaction", *Prac. Natl. Acad. Sci. USA*, Nov. 1985, vol. 82, No. 22, pp. 7686-7690.

Inaba, et al. "Resting and Sensitized T Lymphocytes Exhibit Distinct Stimulatory (Antigen-Presenting Cell) Requirements for Growth and Lymphokine Release", *J. Exp. Med.*, vol. 160, No. 6, Dec. 1, 1984, pp. 1717-1735.

Inaba, et al. "The Function of Ia+ Dendritic Cells and Ia Dendritic Cell Precursors in Thymocyte Mitogenesis to Lectin and Lectin Plus Interleukin 1" *J. Exp. Med.*, vol. 167, Jan. 1988, pp. 149-162.

Inaba, et al. "Generation of Large Numbers of Dendritic Cells From Mouse Bone Marrow Cultures Supplemented With Granulocyte/Macrophage Colony-Stimulating Factor", *J. Exp. Med.*, vol. 176, No. 6, Dec. 1992, pp. 1693-1702.

Iwai, et al. "Acceptance of Murine Thyroid Allografts by Pretreatment of Anti-Ia Antibody or Anti-Dendritic Cell Antibody In Vitro", *Transplantation*, vol. 47, No. 1, Jan. 1989, pp. 45-49.

Jansen, et al. "Inhibition of Human Macrophage Colony Formation by Interleukin-4", *J. Exp. Med.*, vol. 170, Aug. 1989, pp. 577-582.

Jensen, P.E. "Protein Synthesis in Antigen Processing", *The Journal of Immunology*, vol. 141, No. 8, Oct. 15, 1988, pp. 2545-2550.

Jonuleit, et al. "Keratincoyte-Derived IL-15 Enhances Accessory Function of Epidermal Langerhans Cells and Blood Dendritic Cells." *J. Invest. Dermatol.* vol. 105, p. 861, Dec. 1995.

Kampgen, et al. Class II Major Histocompativility Complex Molecules of Murine Dendritic Cells: Synthesis, Sialylation of Invariant Chain, and Antigen Processing Capacity are Downregulated Upon Culture, *Proc. Natl. Acad Sci., USA* 88:3014 1991.

Katz, et al. Epidermal Langerhans Cells are Derived From Cells Originating in Bone Marrow, *Nature*, 282:324 1979.

Kashihara-Sawami, et al. "A Monoclonal Antibody Specifically Reactive to Human Langerhans Cells," *J. Invest. Dermatol.* 87:602-607 1986.

Klinkert, et al. "Accessory and Stimulating Properties of Dendritic Cells and Macrophages Isolated From Various Rat Tissues", *J. Exp. Med.*, vol. 156, No. 1, Jul. 1, 1982, pp. 1-19.

Knight, et al. "Induction of Immune Responses in Vivo With Small Numbers of Veiled (Dendritic) Cells", *Proc.Natl.Acad.Sci.USA*, vol. 80, No. 19, Oct. 1983, pp. 6032-6035.

Knight, et al. "Role of Veiled Cells in Lymphocyte Activation", *European J. Immunology*, vol. 12, (1982), pp. 1057-1060.

Koch, et al. Tumor Necrosis Factor α Maintains the Viability of Murine Epidermal Langerhans Cells in Culture, But in Contrast to Granulocyte/Macrophage Colony-Stimulating Factor, Without Inducing Their Functional Maturation, *J. Exp. Med.*, vol. 171, No. 1, Jan. 1, 1990, pp. 159-171.

Koch, et al. "High Level IL-12 Production by Murine Dendritic Cells: Upregulation Via MHC Class II and CD40 Molecules and Downregulation by IL-4 and IL-10." *Exp. Med.*, vol. 184, pp. 741-746, 1996.

Kraal, et al. Langerhans' Cells Veiled Cells, and Interdigitating Cells in the Mouse Recognized by a Monoclonal Antibody, *J. Exp. Med.*, vol. 163, No. 4, Apr. 1, 1986, pp. 981-997.

Lanzavecchia "Identifying Strategies for Immune Intervention", *Science*, vol. 260, May 14, 1993, pp. 937-944.

Larsen, et al. "Regulation of Immunostimulatory Function and Costimulatory Molecule (B7-1 and B7-2) Expression on Murine Dendritic Cells", *Am. Assoc. Immunologists*, 1994, pp. 5207-5219.

Lechler, et al. Restoration of Immunogenicity to Passenger Cell-Depleted Kidney Allografts by the Addition of Donor Strain Dendritic Cells, *J. Exp. Med.*, vol. 155, Jan. 1982, pp. 31-41.

Lenz, et al. "Human and Murine Dermis Contain Dendritic Cells", *J. Clin. Invest.* 92:2587-2596 Dec. 1993.

Li, et al. Priming With Recombinant Influenza Virus Followed by Administration of Recombinant Vaccine Virus Induces CD8+ T-Coil-Mediated Protective Immunity Against Malaria, *Proc. Natl. Acad. Sci. USA*, vol. 90, pp. 5214-5218, Jun. 1993.

Li, et al. "Influenza A Virus Transfectants With Chimeric Hemagglutinins Containing Epitopes From Different Subtypes", *Journal of Virology*, vol. 66, No. 1., pp. 399-404, Jan. 1992.

Lu, et al. "Propagation of Dendritic Cell Progenitors From Normal Mouse Liver Using Granulocyte/Macrophage Colony-Stimulating Factor and Their Maturational Development in the Presence of Type-1 Collagen", *J. Exp. Med.*, vol. 179, Jun. 1994, pp. 1823-1834.

Luytjes, et al. "Amplification, Expression, and Packaging of a Foreign Gene by Influenza Virus", *Cell*, vol. 59, pp. 1107-1113, Dec. 22, 1989.

Macatonia, et al. "Primary Stimulation by Dendritic Cells Induces Antiviral Proliferative and Cytotoxic T Cell Responses in Vitro" *Journal of Experimental Medicine*, vol. 169, Apr. 1989, pp. 1255-1264.

Macatonia, et al. "Localization of Antigen on Lymph Node Dendritic Cells After Exposure to the Contact Sensitizer Fluorescein Isothiocyanate", *J.Exp.Med.*, vol. 166, Dec. 1987, pp. 1654-1667.

MacPherson "Lymphoid Dendritic Cells: Their Life History and Roles in Immune Responses", *Res. Immunology*, 1989, vol. 140, pp. 877-926.

MacPherson, et al. "Properties of Lymph-Borne (Veiled) Dendritic Cells in Culture", *Immunology*, vol. 68, No. 1, Sep. 1989, pp. 108-113.

MacPherson, et al. "Endotoxin-Mediated Dendritic Cell Release From the Intestine: Characterization of Released Dendritic Cells and TNF Dependence.", *J. Immunol.* vol. 154, pp. 1317-1322, (1995).

Markowicz "Granulocyte-Macrophage Colony-Stimulating Factor Promotes Differentiation and Survival of Human Peripheral Blood Dendritic Cells in Vitro", *J. Clin. Invest.*, vol. 85(3), Mar. 1990, p. 955-961.

Mason, et al. "The Rat Mixed Lymphocyte Reaction: Roles of a Dendritic Cell in Intestinal Lymph and T-Cell Subsets Defined by Monoclonal Antibodies", *Immunology*, vol. 44, No. 1, Sep. 1981, pp. 75-87.

Mayani, et al. "Cytokine-Induced Selective Expansion and Maturation of Erythroid Versus Myeloid Progenitors From Purified Cord Blood Precursor Cells", *Blood*, vol. 81, No. 12, Jun. 15, 1993, pp. 3252-3258.

Mayordomo, et al. "Bone Marrow-Derived Dendritic Cells Pulsed With Synthetic Tumour Peptides Elicit Protective and Therapeutic Antitumor Immunity." *Nature Med.* vol. 1, No. 12, pp. 1297-1302, Dec. 1995.

McWilliam, et al. "Rapid Dendritic Cell Recruitement is a Hallmark of the Acute Inflammatory Response at Mucosal Surfaces." *J. Exp. Med.* vol. 179, pp, 1331-1336, Apr. 1994.

Metcalf, D. "The Molecular Control of Blood Cells", *Harvard Univ. Press*, Cambridge, MA 1988.

Metcalf, D. "The Molecular Control of Cell Division Differentiation Commitment and Maturation in Haemopoietic Cells", *Nature*, 339:27-30 1989.

Metcalf, D. "Control of Granulocytes and Macrophages: Molecular, Cellular and Clinical Aspects", *Science* 254:529-533 1991.

Metlay, J.P., et al. "The Distinct Leukocyte Integrins of Mouse Spleen Dendritic Cells as Identified With New Hamster Monoclonal Antibodies", *J. Exp. Med.* 171:1753-1771, 1990.

Mohamadzadeh, et al. "Functional Andmorphological Characterization of 4F7+ Spleen Accessory Dendritic Cells", *Inter. Immun.* 5/6:615-624.

Mukherji, et al. "Induction of Antigen-Specific Cytolytic T Cells in Situ in Human Melanoma by Immunization With Synthetic Peptide-Pulsed Autologous Antigen Presenting Cells", *Proc. Natl. Acad. Sci., USA*, vol. 92, pp. 8078-8082, Aug. 1995.

Naito, et al. "Macrophage Factors Which Enhance the Mixed Leukocyte Reaction Initiated by Dendric Cells", *Journal of Immunology*, vol. 142, No. 6, Mar. 15, 1989, pp. 1834-1839.

Nonacs, et al. Mechanisms of Mouse Spleen Dendritic Cell Function in the Generation of Influenza-Specific, Cytolytic T Lymphocytes, *J. Exp. Med.* vol. 176, Aug. 1992, pp. 519-529.

Nussenzweig, M.C., et al. "A Monoclonal Antibody Specific for Mouse Dendritic Cells", *Proc. Natl. Acad. Sci. USA* 79:161-165, 1982.

O'Doherty, et al. "Human Blood Contains Two Subsets of Dendritic Cells, One Immunologically Mature and the Other Immature", *Immunology*, vol. 82, 1994, pp. 487-493.

Osband, et al., "Problems in the Investigational Study and Clinical Use of Cancer Immunotherapy", Immunology Today, vol. 11. No. 6, pp. 103-105, 1990.

Paglia, et al. "Immortalized Dendritic Cell Line Fully Competent in Antigen Presentation Initiates Primary T Cell Responded in In Vivo", *J. Exp. Med.*, vol. 178, Dec. 1993, pp. 1893-1901.

Peace, et al., "Lysis of RAS Oncogene-Transformed Cells by Specific Cytotoxic T Lymphocytes Elicited by Primary in Vitro Immunization With Mutated RAS Peptide", *J. Exp. Med.*, vol. 179, Feb. 1994, pp. 473-479.

Pugh, et al. "Characterization of Nonlymphoid Cells Derived From Rat Peripheral Lymph", *J. Exp. Med.*, 157:1758 1983.

Puré, et al. "Antigen Processing by Epidermal Langerhans Cells Correlates With the Level of Biosynthesis of Major Histocompatibility Complex Class II Molecules and Expression of Invariant Chain", *J. Exp. Med.*, 172:1459 1990.

Pettengell, et al. "Peripheral Blood Progenitor Cell Transportation in Lymphoma and Leukemia Using a Single Apheresis", *Blood*, vol. 82, No. 12, Dec. 15, 1993, pp. 3770-3777.

Reid, et al. "Interactions of Tumor Necrosis Factor With Granulocyte-Macrophage Colony-Stimulating Factor and Other Cytokines in the Regulation of Dendritic Cell Growth in Vitro From Early Bipotent CD34 Progenitors in Human Bone Marrow", *J. Immunology*, vol. 149, No. 8, Oct. 15, 1992, pp. 2681-2688.

Ria, et al. "Immunological Activity of Covalently Linked T-Cell Epitopes", *Nature*, vol. 343, Jan. 25, 1990, pp. 381-383.

Riddell, et al. "Restoration of Viral Immunity of Immunodeficient Humans by the Adaptive Transfer of T Cell Clones", *Science*, vol. 257, pp. 238-241, Jul. 10, 1992.

Roake, et al. "Dendritic Cell Loss From Non-Lymphoid Tissues After Systemic Administration of Lipopolysaccharide, Tumor Necrosis Factor, and Interleukin-1." *J. Exp. Med.* vol. 181, pp. 2237-2247, Jun. 1995.

Romani, et al. "Generation of Mature Dendritic Cells From Human Blood. An Improved Method With Special Regard to Clinical Applicability", *J. Imm. Meth.* vol. 196, 1996, pp. 137-151.

Romani, et al. "Proliferating Dendritic Cell Progenitors in Human Blood", *J. Exp. Med.*, vol. 180, Jul. 1994, pp. 83-93.

Romani, et al. "Cultured Human Langerhans Cells Resemble Lymphoid Dendritic Cells in Phenotype and Function." *J. Invest. Dermatol.* vol. 93, No. 5, pp. 600-609, Nov. 1989.

Romani, et al. "Presentation of Exogenous Protein Antigens by Dendritic Cells to T Cell Clones: Intact Protein is Presented Best by Immature, Epidermal Langerhans Cells", *J. Exp. Med.*, 169:1169 1989.

Rudensky, et al. "Sequence Analysis of Peptides Bound to MHC Class II Molecules", *Nature*, vol. 353, Oct. 17, 1991, pp. 622-627.

Sallusto, et al. "Dendritic Cells Use Macropinocytosis and the Mannose Receptor to Concentrate Antigen in the MHC Class II Compartment: Downregulation by Cytokines and Bacterial Products." *J. Exp. Med.* vol. 182, pp. 389-400, Aug. 1995.

Santiago-Schwarz, F., Belilos, E., Diamond, B., Carsons SE: (1992) "TNF in Combination With GM-CSF Enhances the Differentiation of Neonatal Cord Blood Stem Cells Into Dendritic Cells and Macrophages." *J. Leukocyte Biol.* 52:274-281 1992.

Scheicher, et al. "Dendritic Cells From Mouse Bone Marrow: in Vitro Differentiation Using Low Doses of Recombinant Granulocyte-Macrophage Colony-Stimulating Factor", *J. Immunological Methods*, vol. 154, No. 2, pp. 253-264, 1992.

Schuler, et al. "Epidermal Langerhans Cells Represent Immature Dendritic Cells That Must Differentiate Prior to Expressing Their Full Immunologic Potential", *Investig. Dermatology*, vol. 87, No. 1, Jul. 1, 1986, p. 116.

Schuler, et al. "Murine Epidermal Langerhans Cells Mature Into Potent Immunostimulatory Dendritic Cells in Vitro", *J. Exp. Med.*, vol. 161, Mar. 1985, pp. 526-546.

Shimonkevitz, et al. "Antigen Recognition by H-2 Restricted Cells", *J. Exp. Med.*, vol. 158, Aug. 1983, pp. 303-316.

Sornasse, et al. "Loading of Dendritic Cells With Antigen in Vitro or in Vivo by Immunotargeting Can Replace the Need for Adjuvant", *Adv. Exp. Med. Biol.*, vol. 329, 1993, pp. 299-303.

Steinman "The Dendritic Cell System and Its Role in Immunogenicity", *Ann. Rev. Immunology*, vol. 9, pp. 271-296, 1991.

Steinman, Identification of a Novel Cell Type in Peripheral Lymphoid Organs of Mice, *J. Exp. Med.*, vol. 149, No. 2, pp. 1-16, Jan. 1979.

Steinman, et al. "Maturation and Migration of Cutaneous Dendritic Cells", *Investig. Dermatology*, vol. 105, No. 1, Jul. 1995, p. 2S-7S.

Steinman, et al. "Identification of a Novel Cell Type in Peripheral Lymphoid Organs of Mice", *J. Exp. Med.*, vol. 137, No. 4, Apr. 1, 1973, pp. 1142-1162.

Steinman "Dendritic Cells: Clinical Aspects", *28th Forum in Immunology*, Rockefeller Univ. and Irgington Inst. for Med. Res., pp. 911-924.

Steinman, et al. "Identification of a Novel Cell Type in Peripheral Lymphoid Organs of Mice", *J. Exp. Med.*, vol. 139 No. 6, Jun. 1, 1974, pp. 1431-1445.

Steinman, R.M., et al. "Lymphoid Dendritic Cells are Potent Stimulators of the Primary Mixed Leukocyte Reaction in Mice", *Proc. Natl. Acad. Sci. USA* 75:5132-5136.

Sprecher, et al. "Role of Langerhans Cells and Other Dendritic Cells in Viral Diseases", *Arch Virol* 132:1-28 1993.

Szabolcs, et al. "Expansion of Immunostimulatory Dendritic Cells Among the Myeloid Progeny of Human CD34+ Bone Marrow Precursors Cultured With C-Kit Ligand, Granulocyte-Macrophage Colony-Stimulating Factor, and TNF-$\alpha^{1,2}$" *J. Immunol.* vol. 154, pp. 5851-5861, (1995).

Teunissen, "Human Epidermal Langerhans Cells Undergo Profound Morphologic and Phenotypical Changes During in Vitro Culture", *J. Invest. Dermatol.*, 94:166 1990.

Thomas, et al. "Isolation and Characterization of Human Peripheral Blood Dendritic Cells." *J. Immunol.* vol. 150, No. 3, pp. 821-834, Feb. 1, 1993.

Thomas, et al. "Rheumatoid Synovium is Enriched in Mature Antigen-Presenting Dendritic Cells." *J. Immunol.* vol. 152, pp. 2613-2623, (1993).

Troppmair, et al. "Interferons (IFNs) and Tumor Necrosis Factors (TNFs) in T Cell-Mediated Immune Responses Against Alloantigens. I. Influence on the Activation of Resting and Antigen-Primed T Cells", *Immunobiology*, vol. 176, pp. 236-254, (1988).

Vakkila, et al. "Human Peripheral Blood-Derived Dendritic Cells Do Not Produce Interleukin 1$\alpha$, Interleukin 1$\beta$, or Interleukin 6", *Scand. J. Immunology*, vol. 31, No. 3, pp. 345-352, 1990.

Van Voorhis, et al. "Human Dendritic Cells", *J. Exp. Med.* vol. 155, Apr. 1982, pp. 1172-1187.

Wang, et al. "Human Tumor Antigens Recognized by T Lymphocytes: Implications for Cancer Therapy", *Journal of Leukocyte Biology*, vol. 60, pp. 296-309, Sep. 1996.

Witmer-Pack, et al. "Granulocyte/Macrophage Colony-Stimulating Factor is Essential for the Viability and Function of Cultured Murine Epidermal Langerhans Cells", *J. Exp. Med.*, vol. 166, No. 5, Nov. 1, 1987, pp. 1484-1498.

Witmer-Pack, M.D., et al. "Macrophages, but Not Dendritic Cells, Accumulate Colloidal Carbon Following Administration in Situ", *J. Cell Sci. 105*:965-973, 1993.

Williams, et al. "Isolation and Function of Human Dendritic Cells, International Review of Cytology", 153:41-103 1994.

Wraith, et al. "Antigen Recognition in Autoimmune Encephalomyelitis and the Potential for Peptide-Mediated Immunotherapy", *Cell*, vol. 59, pp. 247-255, 1989.

Wraith, et al. "Influenza Virus-Specific Cytotoxic T-Cell Recognition: Stimulation Nucleoprotein-Specific Clones With Intact Antigen", *Immunology*, vol. 59, pp. 173-180, 1986.

Young, et al. "Dendritic Cells as Adjuvants for Class I Major Histocompatibility Complex-Restricted Antitumor Immunity", *J. Exp. Med.*, vol. 183, pp. 7-11, Jan. 1996.

Young, et al. Dendritic Cells Stimulate Primary Human Cytolytic Lymphocyte Responses in the Absence of CD4 Helper T Cells, *Journal of Experimental Medicine*, vol. 171, pp. 1315-1332, Apr. 1990.

Young, et al. "Accessory Cell Requirements for the Mixed-Leukocyte Reaction and Polyclonal Mitogens, as Studied With a New Technique for Enriching Blood Dendritic Cells." *Cell. Immunol.*, vol. 111, pp. 167-182.

Young, et al. "Identification of Dendritic Cell Colony-Forming Units Among Normal CD34+ Bone Marrow Progenitors That Are Expanded by *C-Kit-Ligand* and Yield Pure Dendritic Cell Colonies in the Presence of Granulocyte/Macrophage Colony-Stimulating Factor and Tumor Necrosis Factor α." *J. Exp. Med.* vol. 182, pp. 1111-1120, Oct. 1995.

Zhou, et al. "Human Blood Dendritic Cells Selectively Express CD83, a Member of the Immunoglobulin Superfamily", *The Journal of Immunology*, vol. 154, 1995, pp. 3821-3835.

Zhou, et al. "CD14+ Blood Monocytes Can Differentiate Into Functionally Mature CD83+ Dendritic Cells." *Proc. Natl. Acad. Sci. USA*, vol. 93, pp. 2588-2592, Mar. 1996.

Ziegler, et al. "Decrease in Macrophage Antigen Catabolism Caused by Ammonia and Chloroquine is Associated With Inhibition of Antigen Presentation to T Cells", *Proc.Natl.Acac.Sci., USA*, vol. 79, Jan. 1982, pp. 175-178.

Zvaifler, et al. "Identification of Immunostimulatory Dendritic Cells in the Synovial Effusions of Patients With Rheumatoid Arthritis." *J. Clin. Invest.* vol. 76, pp. 789-800, Aug. 1985.

Jacques Banchereau, et al., Immunobiology of Dendritic Cells, Annu. Rev. Immunol. 2000. 18:767-811.

Tseng, Jerming et al., "Suppression of Tumor Necrosis Factor-α, Interleukin-1 β, Interleukin-6 and Granulocyte-Monocyte Colony Stimulating Factor Secretion From Human Monocytes by an Extract of *Poria cocos*", Chinese J. Microbiol. Immunol., 25:1-11 (1992).

Peters, Anke M.J., et al.,"Cytokine Secretion by Peripheral Blood Monocytes From Human Immunodeficiency Virus-Infected Patients Is Normal", Clin. Immunol. and Immunopathol., 61:343-352 1991.

Jenkins, John K.. et al., "Interleukin 1 Receptor Antagonist Production in Human Monocytes is Induced by IL-1 α, IL-3, IL-4 and GM-CSF", Cytokine 5:407-415, (1993).

Xu, Hui et al., "Dendritic Cells Differentiated From Human Monocytes Through a Combination of IL-4, GM-CSF and IFN-γ Exhibit Phenotype and Function of Blood Dendritic Cells", Dendritic Cells in Fundamental and Clinical Immunology vol. 2, Plenum Press, New York 1995, pp. 75-78.

Radmayr C. et al., "Dendritic Antigen-Presenting Cells From the Pheripheral Blood of Renal-Cell-Carcinoma Patients", Int. J. Cancer 63:627-632 (1995).

Milarski, Kim L. et al., "Expression of Human HSP70 During the Synthetic Phase of the Cell Cycle", Proc. Natl. Acad. Sci. USA, 83:9517-9521 (1986).

Najar, H.M. et al. "Differentiation of Human Monocytes Into Accessory Cells at Serum-Free Conditions", Eur. J. Cell Biol: 51(2):339-46 (1990).

Passlick, et al., "Identification and Characterization of a Novel Monocyte Subpopulation in Human Peripheral Blood", *Blood*, vol. 74, No. 7, Nov. 15, 1989; pp. 2527-2534.

Lauener, et al., "Interleukin 4 down-regulates the expression of CD14 in normal human Monocytes" *European Journal of Immunology*, vol. 20, 1990, pp. 2375-2381.

http://www.merckbiosciences.co.uk/html/cbc/proteinA_proteinG_text2.htm.

http://www.merck.biosciences.co.uk/product/507861.

Sornasse et al., Antigen-pulsed Dendritic Cells Can Efficiently Induce an Antibody Response in Vivo, J. Exp. Med 175:15-21 (1992).

\* cited by examiner

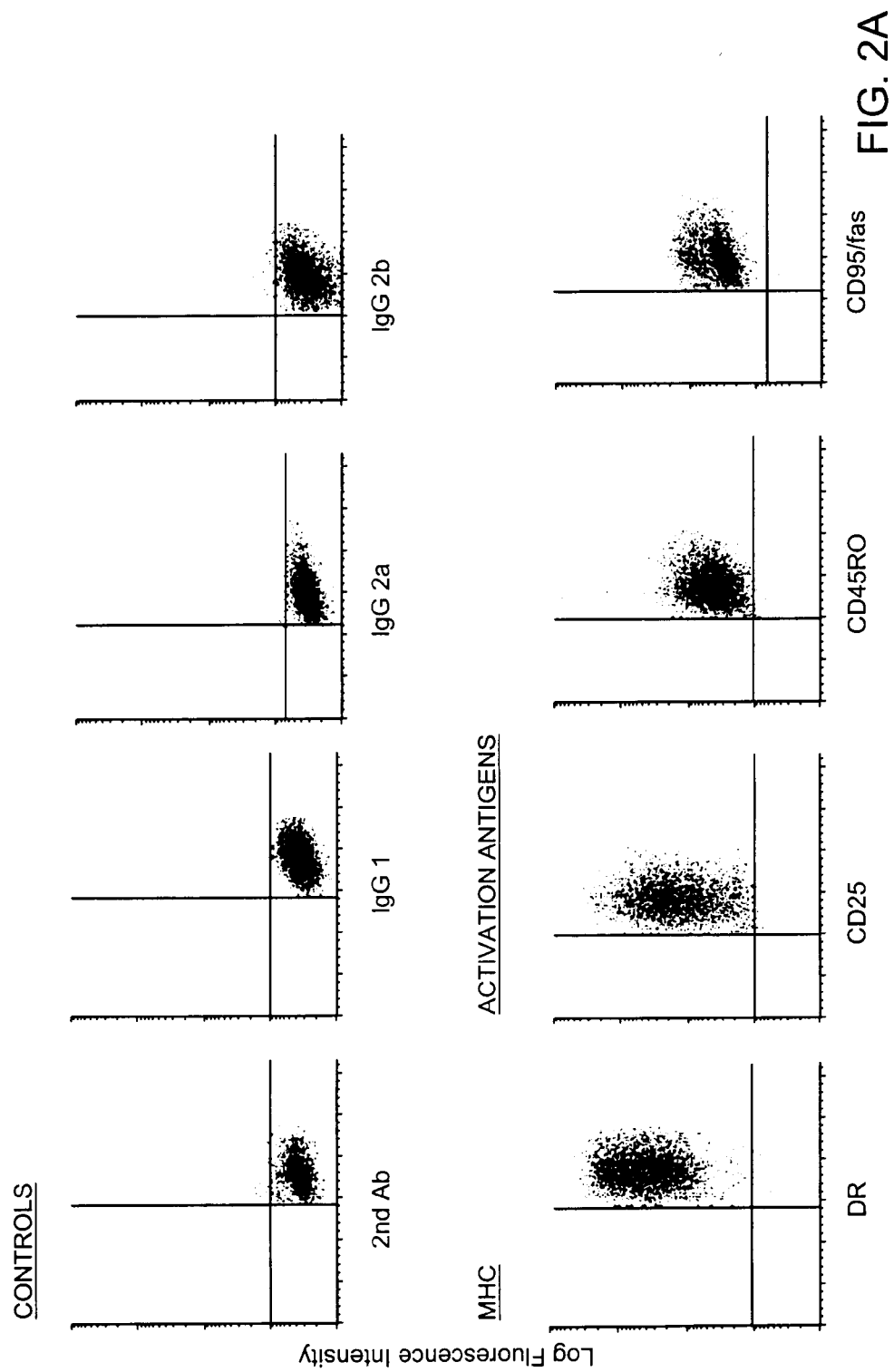

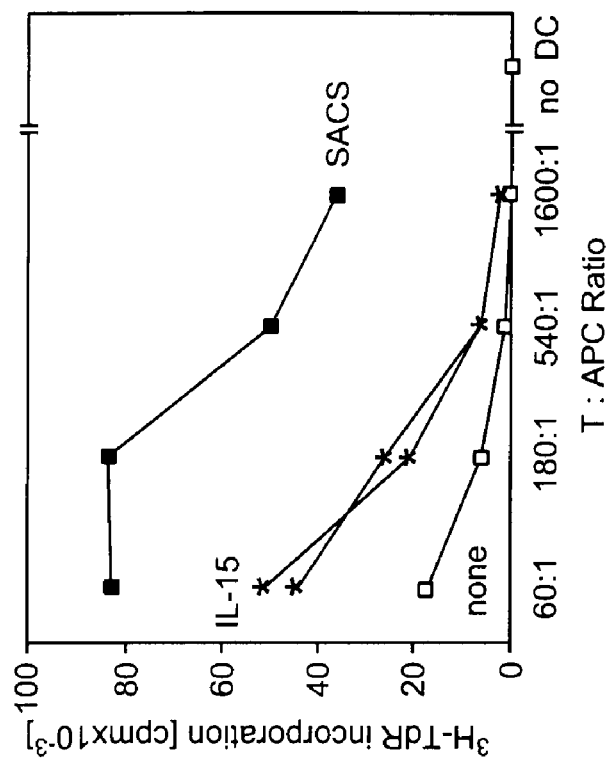
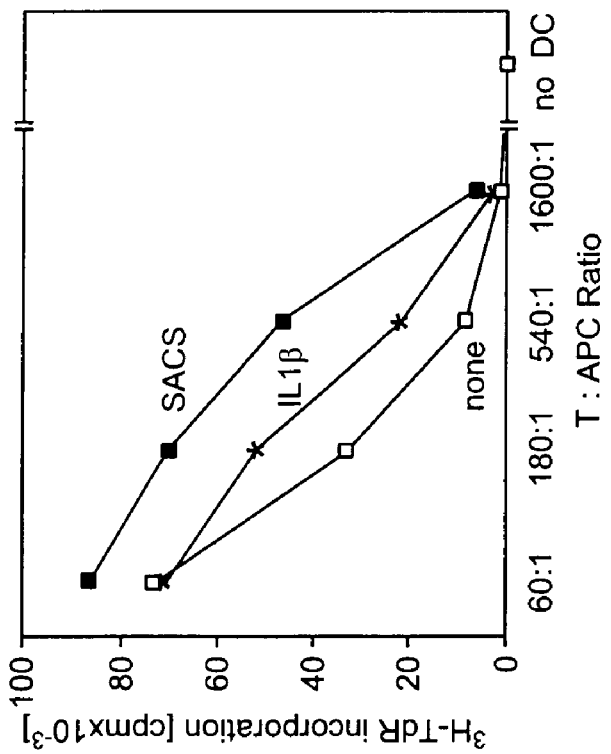
FIG. 8A
FIG. 8B

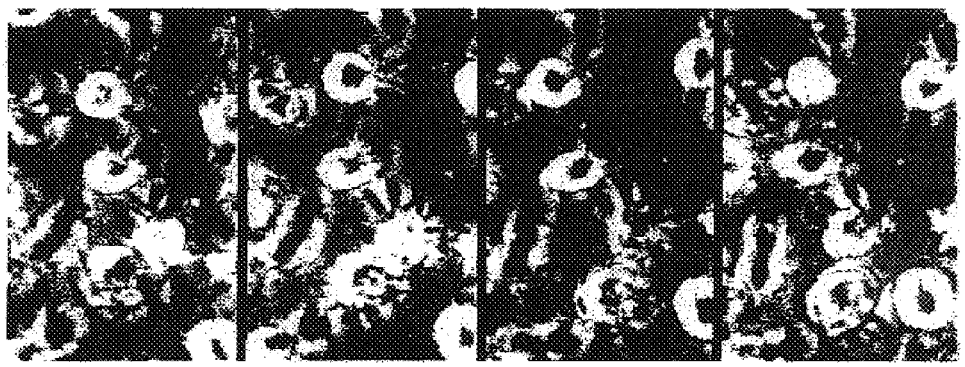
FIG. 9A  FIG. 9B  FIG. 9C  FIG. 9D
FIG. 10A
FIG. 10B

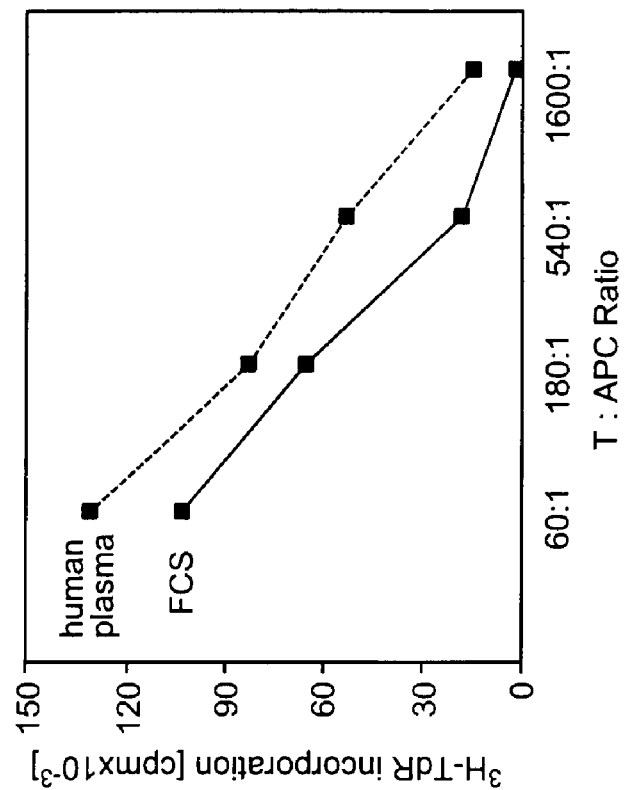
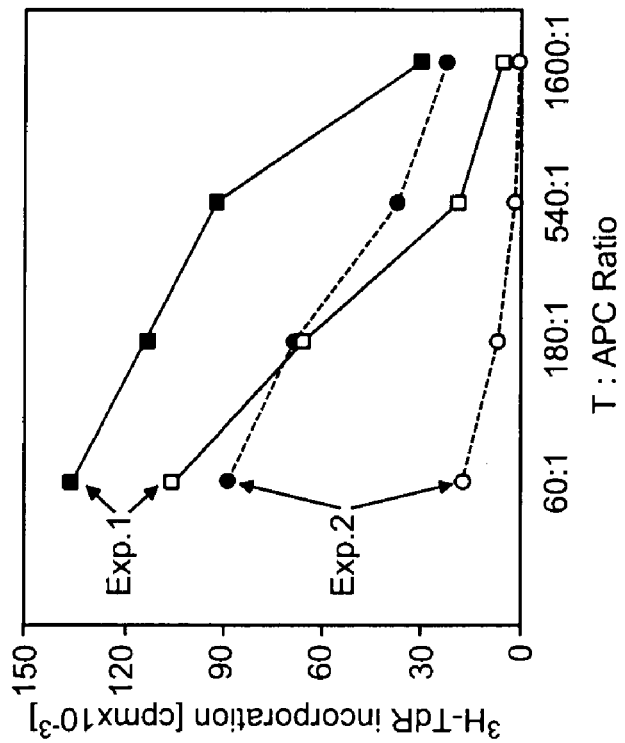
FIG. 11A
FIG. 11B

METHOD AND COMPOSITIONS FOR OBTAINING MATURE DENDRITIC CELLS

This invention was made with United States Government support under NIH grants AR-39552, AR-42557 and AI-24775. The United States Government has certain rights in this invention.

TECHNICAL FIELD OF THE INVENTION

This invention relates to methods and compositions useful for activating cells of the immune system. The methods and compositions provided by this invention are useful for causing the maturation of non-proliferating immature dendritic cells to mature dendritic cells capable of processing and presenting antigen. This invention also relates to culture mediums which promote maturation of immature dendritic cells to mature dendritic cells. In addition, this invention relates to assays useful for detecting the presence in a test substance of a dendritic cell maturation factor.

BACKGROUND OF THE INVENTION

Dendritic cells are specialized antigen presenting cells, critical for eliciting T cell mediated immune responses (Steinman, 1991; Caux et al. 1995a; Hart and McKenzie, 1990; Austyn, 1987). These specialized antigen presenting cells elicit both CD4+ helper cells (Inaba et al. 1990a; Inaba et al. 1990b; Crowley et al. 1990) and CD8+ killer cells (Porgador and Gilboa, 1995; Mayordomo et al. 1995; Zitvogel et al. 1995) in vivo.

Because of the potent activity of dendritic cells to activate T cells, the art, e.g. Flanand et al., *Env. J. Immunol.*, 24:605-610, 1994, has accepted the characterization of dendritic cells as "nature's adjuvant". It is therefore desirable to be able to use dendritic cells to process and present protein antigens as a means of modulating an individual's immune response, and in particular to activate an individual's T cells in connection with the treatment or prevention of disease.

The use of primed dendritic cells to activate cytotoxic T cells has been reported. For example, Paglia et al., recently reported that murine dendritic cells cultured from bone marrow precursors and exposed to antigen in vitro provide effective resistance to challenge with live tumor cells. Paglia et al., "Murine Dendritic Cells Loaded In Vitro With Soluble Protein Prime Cytotoxic T Lymphocytes Against Tumor Antigen In Vivop", *J. Exp. Med.*, 183:317-322 (1996).

The in vitro observations and the murine results have recently been extended to the treatment of humans with B cell lymphoma using mature dendritic cells which were primed in vitro with tumor antigens. Hsu et al., "Vaccination of Patients With B-cell Lymphoma Using Autologous Antigen-Pulsed Dendritic Cells", *Nature Med.*, 2:52-58 (1996). According to this report, the antigen used to prime the dendritic cells was idiotypic antibody obtained from hybridomas made from the fusion of lymph node tumor cells with a mouse cell line. All of the four patients involved in this study exhibited significant antitumor idiotype PBMC proliferative responses. Positive clinical responses were also observed including one patient who experienced complete tumor regression. Hsu et al., however, express uncertainty whether dendritic cells obtained from expansion of dendritic cell cultures in the presence of GM-CSF, TNF-α or IL-4 would function equivalently in their ability to process and present antigen or to stimulate cellular immune responses as the freshly isolated cells.

Prior studies have identified proliferating dendritic cell progenitors within the small CD34+ subfraction of cells in human blood (Inaba et al. 1992; Caux et al. 1994; Caux et al. 1992; Caux et al. 1995). Methods have been developed for expanding these proliferating cells in culture to obtain sufficient numbers of cells to be useful for priming with antigen and administering to an individual to activate an immune response. Steinman et al. International patent application WO 93/20185. These dendritic cells can be stimulated with cytokines, particularly GM-CSF and, optionally TNFα or other cytokines, to develop into potent dendritic cells over 1-2 weeks in culture (Caux et al. 1992; Inaba et al. (1992)). Although useful dendritic cells can be produced from the proliferating precursors, it is desirable to obtain alternative methods of obtaining suitable numbers of mature dendritic cells for therapeutic purposes where proliferating progenitors are infrequent.

The removal of monocytes and lymphocytes from human blood has uncovered a small population of nonproliferating progenitors that require cytokines to develop into typical dendritic cells. These progenitor cells exist at a concentration of at most about $10^6$ cells per 450-500 ml of blood (O'Doherty et al. 1994; O'Doherty et al. 1993; Thomas et al. 1993). More recently, the combination of GM-CSF and IL-4 has been shown to facilitate the generation of significantly larger numbers of dendritic cells from adherent blood mononuclear fractions, about $3-8\times10^6$ per 40 ml of blood (Romani et al. 1994; Sallusto and Lanzavecchia, 1994 both of which are incorporated herein by reference). However, we have now determined that when the cytokines are removed, the cells revert to an adherent and less stimulatory state, that is, they do not have the properties of mature, stable dendritic cells. If the latter reversion were to take place in vivo during adoptive immunotherapy, the cells could be ineffective as adjuvants. In addition, it is desirable to develop a culture system independent of fetal calf serum.

Engleman et al. International Patent Application WO 95/34638 refers to a method of activating an immune response in a human patient by administering to the patient dendritic cells primed with antigen. Engleman et al. however refer to using dendritic cells isolated from the individual which exist in small numbers. Accordingly, it would be desirable to be able to obtain dendritic cells from a large population of cells present in an easily accessible tissue such as blood.

Two antigens, have recently been reported which, in addition to other antigens or phenotypic characteristics, distinguish mature dendritic cells from other types of white blood cells. Zhou and Tedder (Zhou and Tedder, 1995) reported that CD83, a member of the immunoglobulin superfamily that was cloned from an EBV induced B cell library, is expressed on dendritic cells in blood cells that were cultured for 2 days. This culture period is sufficient to allow a small subset of immature dendritic cells to mature (O'Doherty et al. 1993). CD83 has also been detected on some presumptive dendritic cells in the T cell areas of lymphoid organs, and on some B cells in germinal centers (Zhou et al. 1992). Langhoff and coworkers found that p55, an actin bundling protein, also marks the dendritic cells that are found in 2 day cultures of human blood (Mosialos et al. 1995). p55 is an intracellular protein that was discovered as an EBV induced host cell product. It is expressed by interdigitating cells and at high levels in the brain (Mosialos et al. 1995).

SUMMARY OF THE INVENTION

This invention provides methods of preparing large numbers of stable, mature dendritic cells. The stable mature dendritic cells provided by this invention retain characteristics of a mature phenotype, including expression of dendritic cell markers p55 and CD83 and high levels of accessory molecules like CD86 and CD40, even when removed from contact with cytokines which promote the maturation of pluripotential peripheral blood mononuclear cells (PBMCs) to non-stable immature dendritic cells. As used herein, "stable" refers to retention of a mature dendritic cell phenotype for three days when mature dendritic cells are cultured in the absence of cytokines. Dendritic cells are considered "mature" according to this invention when they have an increased expression of one or more phenotypic markers, such as for example non-adherence to plastic and CD86 or other antigen markers, associated with the accessory function of dendritic cells following contact with a dendritic cell maturation factor.

In one embodiment of the invention, mature dendritic cells are produced in vivo or in vitro from immature dendritic cells derived from PBMC pluripotential cells having the potential of expressing either macrophage or dendritic cell characteristics. The method, according to the invention, comprises contacting the immature dendritic cells with a dendritic cell maturation factor. The dendritic cell maturation factor, may actually be one or more different substances, and may be provided by substances including, but not limited to PBMC conditioned media, maturation factors purified from the conditioned medium, and SACS (fixed *Staphylococcus aureus* Cowan 1 strain (Pansorbin)). Culture of the pluripotential cells with cytokines such as for example, a combination of GM-CSF and IL-4 or IL-13 stimulates the differentiation of the pluripotential cells to immature dendritic cells.

The method provided by this invention is particularly useful with human cells and provides sufficient numbers of mature dendritic cells to be useful for priming with antigen in vitro and activating an individual's T cells by administering the primed dendritic cells to the individual, or activation of T cells in vitro which are then administered to the individual. Accordingly, another aspect of this invention is a method of activating an individual's T cells comprising:

a) obtaining a population of pluripotential cells having the potential of expressing either macrophage or dendritic cell characteristics from an individual and placing them in culture;

b) contacting the pluripotential cells of step a with at least one cytokine to produce immature dendritic cells;

c) contacting the immature dendritic cells with a dendritic cell maturation factor for a time sufficient to cause said immature dendritic cells to stably express dendritic cell characteristics;

d) contacting the dendritic cells obtained from step c with an antigen to produce primed dendritic cells;

e) exposing T cells to the primed dendritic cells of step d to activate said T cells. It is to be understood that one or more of the above steps may be combined so as to occur concurrently, such as for example, steps c and d.

Activation of T cell responses against a wide variety of antigens is facilitated by this invention. Such antigens include, but are not limited to viral, bacterial, tumor and self antigens such as antigen receptors, e.g. T cell receptors. Accordingly, the dendritic cells prepared according to this invention are useful for the prevention and treatment of various diseases including infectious disease, cancer and autoimmune disease.

The methods of promoting maturation of dendritic cells to mature dendritic cells using cytokines and a dendritic cell maturation factor, and the subsequent activation of T cells, may also be applied to individuals in vivo. According to this embodiment, an individual may be administered cytokines, e.g. GM-CSF and IL-4, or G-CSF to stimulate in vivo the production of immature dendritic cells. A dendritic cell maturation factor, such as conditioned medium, or a substance which stimulates the release of a dendritic cell maturation factor from PBMCs, may also be administered to an individual to stimulate in vivo maturation of immature dendritic cells, the population of which may optionally have been increased through prior administration of cytokines.

This invention also encompasses the mature dendritic cells prepared according to the method of the invention and pharmaceutical compositions comprising the mature dendritic cells and a physiological carrier. Such carriers may include the media described below.

Another aspect of this invention is a culture medium useful for causing the maturation of immature dendritic cells to phenotypically stable, mature dendritic cells. The culture medium of the invention comprises a mixture of salts, carbohydrates and vitamins at physiologic concentrations typical of commercially available culture medium; as well as about 1-5%, and more preferably 1% human serum or plasma; GM-CSF and one or more cytokines which promote maturation of the PBMC phenpotential cells to immature dendritic cells and in amounts together sufficient to promote maturation of pluripotential PBMC to immature dendritic cells; and a sufficient concentration of a dendritic cell maturation factor to cause the maturation of immature dendritic cells to stable mature dendritic cells. This method can also be used with serum-free medium such as for example, XVIVO-20 or AIM-V.

Another aspect of this invention is an assay to detect a dendritic cell maturation factor. Such an assay is useful for the identification and production of the factor present in PBMC conditioned medium which causes the maturation of immature dendritic cells to the mature dendritic cells provided by this invention. This assay comprises contacting a test sample with a culture of unstable, immature dendritic cells derived from a population of pluripotential cells having the potential of expressing either macrophage or dendritic cell characteristics and which express characteristics of immature dendritic cells when cultured in a medium containing at least one cytokine. The presence of a dendritic cell maturation factor in the test substance is then determined by detecting the maturation of the immature dendritic cells in response to the test substance.

It is an object of this invention to provide methods and compositions useful for activating an individual's T cells against specific antigens. The activation of an individual's T cell is useful for the prevention or treatment of disease, for example killer cells to treat or vaccinate against cancer or infection.

It is another of this invention to provide methods useful for causing the stable maturation of immature dendritic cells to mature dendritic cells suitable for administering to an individual for the purpose of activating their immune response, and in particular, T cells.

Another object of this invention is to provide mature dendritic cells cultured in vitro from non-proliferating pluripotential cells.

Another object of this invention is to provide culture mediums which promote the maturation of immature dendritic cells to stable mature dendritic cells.

Yet another object of this invention is to provide an assay useful for detecting the presence in a test sample of a dendritic cell maturation factor.

Another object of this invention to provide methods for stimulating the maturation of dendritic cells in vivo.

BRIEF DESCRIPTION OF THE FIGURES

FIG. 8: Fixed staphylococci [SACS] are required to ensure the maturation of dendritic cells from progenitor cells. Lymphocyte-depleted PBMC were cultured for 7 days in RPMI medium supplemented with FCS and GM-CSF/IL-4. Cells were then transferred to fresh plates and cultured for 3 more days in the presence [closed squares] or absence [open squares] of SACS. T cell stimulatory function in the primary allogeneic MLR of the dendritic cells matured in SACS containing medium is markedly enhanced. Neither IL-1β [in A] nor IL-15 [in B] that were given instead of SACS could fully reconstitute the effect.

FIG. 9: Morphology and motility of mature dendritic cells grown in the presence of GM-CSF/IL-4 and CM. Dendritic cell progenitors were primed for 7 days in the presence of GM-CSF and IL-4 followed by a 3 day maturation period in the presence of CM. Culture medium was RPMI supplemented with 1% autologous human plasma. Note the numerous thin cytoplasmic processes ("veils"). Photographs of the same field taken at intervals of 15 seconds show that the veils move. Magnification: ×550.

FIG. 10: Phagocytosis of latex beads. Dendritic cells were grown in the presence of GM-CSF and IL-4 until day 8. GCS-containing RPMI medium was used. Cells in the upper panel were exposed to latex beads for 24 hours in the absence of CM. Latex is taken up into the cells (arrows). In the lower panel cells were first allowed to mature in the presence of CM from day 7 to day 10 and were then exposed to latex. Little or no latex is phagocytosed into mature, "veiled" cells. Only a contaminating adherent cell has accumulated beads. ×300.

Tetanus toxoid protein [1 μg/ml] is presented to a peptide-specific T cell clone. CM-induced maturation leads to a decrease in antigen processing capacity. Triangles in D indicate the [lack of] response of clone cells to APC in the absence of antigen. Values are means of triplicate wells and are expressed as cpm×10$^{-3}$. [E,F] Peptide-pulsed mature dendritic cells elicit T cell lines that lyse autologous target cells in a peptide dose-dependent [E] and MHC-restricted [F] manner. anti-cl. II, anti-cl. I, anti-MHC class II and I mAb's W6/32 and L243, respectively.

Figure 12:
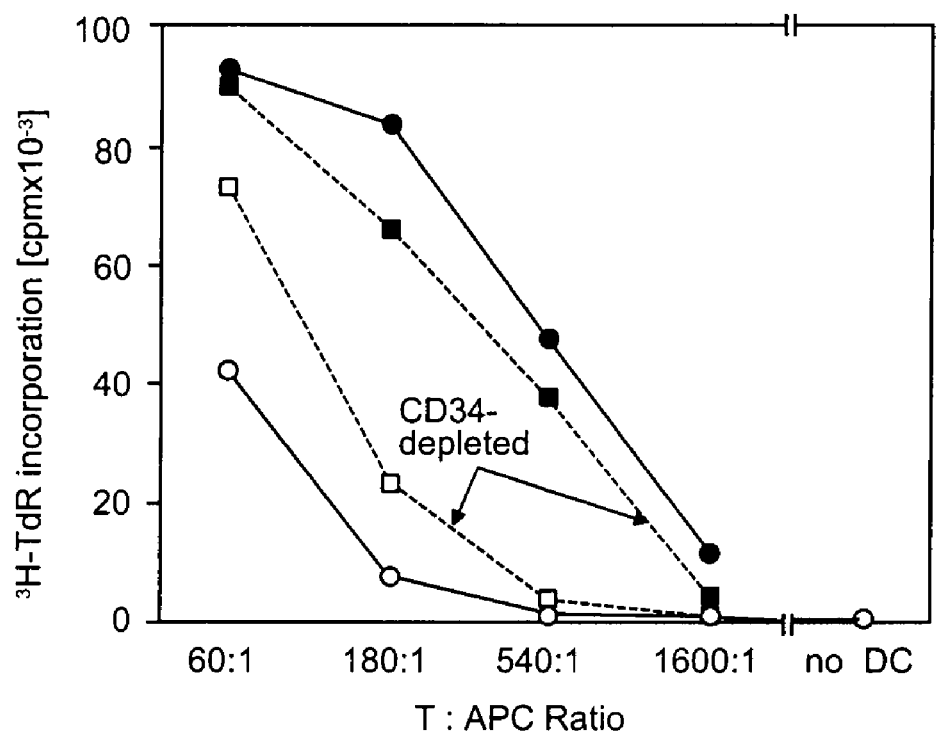

FIG. 12: Dendritic cell progenitors reside in a CD34-negative population. PBMC of a cancer patient who had been treated with G-CSF were passed through an anti-CD34 immunoaffinity column. The original unseparated population [solid lines] and the CD34-depleted population [dashed lines] were cultured in RPMI\FCS with GM-CSF and IL-4 until d7 and further on from d7 to d10 in the presence [closed symbols] or absence [open symbols] of CM. Both populations gave rise to dendritic cells that matured upon exposure to CM.

DETAILED DESCRIPTION OF THE INVENTION

This invention relates to methods and compositions useful for promoting the maturation of immature dendritic cells to a mature and stable phenotype as well as to the stable mature dendritic cells. The mature dendritic cells are useful as antigen presenting cells (APCs) which activate other immune cells including antigen specific helper and killer T cells. Thus, this invention also provides methods and compositions useful for the treatment of disease.

The method of producing mature dendritic cells according to this invention comprises contacting immature dendritic cells with a dendritic cell maturation factor. We have found such a dendritic cell maturation factor in conditioned medium obtained from cultures of peripheral blood mononuclear cells (PBMCs). Immature dendritic cells may be derived from PBMCs by culturing PBMCs with cytokines, such as, for example, a combination of GM-CSF and IL-4, which promote their differentiation to immature dendritic cells. Surprisingly, we have determined that unless they are exposed to a dendritic cell maturation factor, removal of the cytokines from contact with the cells causes the cells to revert back to a pluripotential cell having characteristics similar to macrophages.

The response of immature dendritic cells to contact with the maturation factor is an increased expression of CD83 and p55 dendritic cell markers; strong expression of antigen presenting MHC class I and II products; and expression of several accessory (adhesion and co-stimulatory) molecules including CD40, CD54, CD58, CD80 and CD86. A decrease in expression of CD115 as well as CD14, CD68 and CD32, which are markers associated with immature dendritic cells, is also observed as a result of carrying out the method of this invention. In addition, this phenotype remains stable for up to three days even after removal of cytokines used to promote cell maturation.

Sources of Pluripotential Cells

The pluripotential cells, from which the immature dendritic cells for use in this invention are derived, are present in blood as PBMCs. Although most easily obtainable from blood, the pluripotential cells may also be obtained from any tissue in which they reside, including bone marrow and spleen tissue. These pluripotential cells typically express CD14, CD32, CD68 and CD115 monocyte markers with little or no expression of CD83, p55 or accessory molecules such as CD40 and CD86. When cultured in the presence of cytokines such as a combination of GM-CSF and IL-4 or IL-13 as described below, the pluripotential cells give rise to the immature dendritic cells.

Methods of obtaining PBMCs from blood, such as differential sedimentation through an appropriate medium, e.g. Ficoll-Hypaque [Pharmacia Biotech, Uppsala, Sweden], are well known and suitable for use in this invention. In a preferred embodiment of the invention, the pluripotential cells are obtained by depleting populations of PBMCs of platelets, and T and B lymphocytes. Various methods may be used to accomplish the depletion of the non-pluripotential cells. According to one method, immunomagnetic beads labelled with antibodies specific for T or B lymphocytes, either directly or indirectly may be used to remove the T and B cells from the PBMC population. T cells may also be depleted from the PBMC population by resetting with neuramimidase treated red blood cells as described by O'Dherty (1993), which is incorporated herein by reference.

To produce 3 million mature dendritic cells, it is necessary to process about 40 mls of blood. 4 to 8×10$^7$ pluripotential PBMC give rise to approximately 3 million mature dendritic cells.

Culture of Pluripotenial PBMCs to Produce Immature Dendritic Cells

The immature dendritic cells for use in this invention are post-mitotic but not yet terminally differentiated to either a macrophage or dendritic cell phenotype. Cultures of immature dendritic cells may be obtained by culturing the pluripotential cells in the presence of cytokines which promote their differentiation. A combination of GM-CSF and IL-4 at a concentration of each at between about 200 to about 2000 U/ml, more preferably between about 500 and 1000 U/ml, and most preferably about 800 U/ml (GM-CSF) and 1000 U/ml (IL-4) produces significant quantities of the immature dendritic cells. A combination of GM-CSF (10 ng/ml) and IL-4 (10-20 ng/ml) has been found to be useful with this invention. It may also be desirable to vary the concentration of cytokines at different stages of the culture such that freshly cultured cells are cultured in the presence of higher concentrations of IL-4 (1000 U/ml) than established cultures (500 U/ml IL-4 after 2 days in culture). Other cytokines such as IL-13 may be found to substitute for IL-4.

Methods for obtaining these immature dendritic cells from adherent blood mononuclear fractions are described in Romani et al. (1994); and Sallusto and Lanzavecchia, 1994) both of which are incorporated herein by reference. Briefly, lymphocyte depleted PBMCs are plated in tissue culture plates at a density of about 1 million cells/cm$^2$ in complete culture medium containing cytokines such as GM-CSF and IL-4 at concentrations of each at between about 800 to 1000 U/ml and IL-4 is present at about 1000 U/ml.

Various mediums are suitable to initially culture PBMCs. Typical media for use in this invention comprise physiologic inorganic salts, carbohydrates including sugars, amino acid, vitamins and other components known to those in the art. Preferred media formulations include, for example, RPMI 1640, X-VIVO 20, AIM-V, Hybricare and Iscove's. More preferably the medium is RPMI 1640 or X-VIVO 20 or AIM-V. Most preferably, the medium is RPMI 1640.

It is desirable to avoid the use of fetal calf serum (FCS) in cultures for human use. The presence of bovine proteins may cause unwanted sensitization of the recipient against bovine proteins and it is therefore desirable to substitute FCS with human serum or plasma in an amount sufficient to maintain cell viability. The use of autologous, non-heat-inactivated human plasma at a concentration of about 1% is preferred.

Using RMPI 1640 supplemented with 1% autologous human plasma, a final yield of between about 0.8 to $3.3 \times 10^6$ CD83+ mature dendritic cells is obtainable from 40 ml of blood.

Another source of immature dendritic cells are cultures of proliferating dendritic cell precursors prepared according to the method described in Steinman et al. International application PCT/US93/03141, which is incorporated herein by reference. Since the dendritic cells prepared from the CD34+ proliferating precursors mature to dendritic cells expressing mature characteristics it is likely that they also pass through a development stage where they are pluripotential. By treating these cultures with a dendritic cell maturation factor as described below, the efficiency of obtaining mature dendritic cells from proliferating precursors may also be improved.

Maturation of Immature Dendritic Cells

The mature dendritic cells are prepared according to this invention by contacting the immature dendritic cells with a dendritic cell maturation factor. As referred to herein, the dendritic cell maturation factor may actually be one or more specific substances which act in concert to cause the maturation of the immature dendritic cells. Such a factor has been determined to be present in PBMC conditioned medium, preferably monocyte conditioned medium. Another means of obtaining dendritic cell maturation factors are to treat PMBCs with substances which stimulate the release of such factors. Substances such as immunoglobulin or SACS (also referred to as Pansorbin) are useful for causing monocytes to release cytokines.

After the cells have been cultured for a sufficient time to express some characteristics of dendritic cells, preferably about 6 to 10 days, PBMC conditioned media is added to the culture medium at a final concentration of between about 10 to 50%. More preferably between about 25 and 50%. Maturation of the immature dendritic cells to the mature phenotype may occur without the presence in the medium of the cytokines used to stimulate maturation of the pluripotential cells to immature dendritic cells. Typically, the immature dendritic cells are obtained after about 6 to 7 days in culture with the cytokines. Preferably the immature dendritic cells are subcultured prior to addition of the dendritic cell maturation factor, e.g., conditioned medium.

In a preferred embodiment, the immature dendritic cells which are non-adherent cells are harvested and subcultured in the presence of the dendritic cell maturation factor present in the conditioned medium, and optionally with cytokines such as GM-CSF and IL-4. The mature dendritic cells are typically obtained within approximately three days following addition of the conditioned medium.

Variations in the culture protocol which are also considered within the scope of this invention may include, but not be limited to, changes in cytokines used to promote differentiation of PBMCs to immature dendritic cells, concentrations of cytokines and timing of the addition of the dendritic cell maturation factor present in the conditioned medium.

Characterization of Conditioned Medium

The conditioned medium for use in this invention may be made by culturing PBMCs, preferably monocytes in basic growth medium. Preferably the cells for producing conditioned medium are cultured in the presence of a stimulus which stimulates the release of factors from the donor cells. An example of such a preferred factor is gamma globulin when bound to the culture substrate. Methods for producing PBMC (monocyte) conditioned medium have previously been described in O'Doherty et al. (1993 and 1994) which are incorporated herein by reference. PBMC or preferably T cell depleted, or more preferably T and B cell depleted are cultured (about $5 \times 10^7$ cells/100 mm plate) for about 24 hours in medium (6-8 mls) containing 1% of plasma, preferably autologous plasma. Where conditioned medium is to be used for stimulating maturation of dendritic cells in vivo, the growth medium should be selected to be compatible with use in humans, e.g. X-VIVO or AIM-V and preferably is used without serum or plasma. For use in humans the conditioned medium is concentrated using standard procedures and adjusted to be isotonic so as to be suitable for administration in vivo. Using this method, equivalent concentrations of dendritic cell maturation factor can be achieved in vivo, as in vitro.

In addition to gamma globulin as a stimulant of cytokine release from the culture PBMCs, other cytokine stimulators such as SACS (fixed *Staphylococcus Aureus* Cowan 1 strain, 2.01 mg/ml Ig-binding capacity: Pansorbin cells, Cat. No. 507861) may also be used. Because SACS is bacterially derived its use is less desirable than Ig.

In addition to stimulating the production of cytokines for producing conditioned medium, SACS may also be substituted for conditioned medium as a dendritic cell maturation factor. When used to promote maturation of the immature dendritic cells, SACS is added to cultures at a concentration sufficient to cause their maturation, preferably at about 1:10000 dilution.

This invention provides evidence for a new pathway for dendritic cell development. Prior studies have indicated that dendritic cells arise either from CD34+ proliferating progenitors (Inaba et al. 1992; Caux et al. 1992), or from nonproliferating "null" cells that lack monocyte and lymphocyte markers [CD3, CD14, CD16, CD19](O'Doherty et al. 1993). Both of these progenitor populations are infrequent in human blood representing <0.1% and <1% of blood mononuclear cells, respectively. Sallusto and Lanzavecchia [personal communication] reason that monocytes can give rise to dendritic cells in the presence of FCS, but we find that these cells are not fully mature in several respects. In contrast, large numbers of mature dendritic cells can develop, and in human plasma or serum, when CM is added to the GM-CSF and IL-4 priming step. The precursors are radioresistant and primarily in the standard "monocyte" fraction [CD14 positive and plastic adherent]. It is possible that most monocytes are bipotential and can develop into either macrophages or dendritic cells depending upon the cytokines that are applied. Alternatively, only some of the "monocyte" fraction may have the potential to develop into dendritic cells. At this time, our data are consistent with the latter possibility since the total yield of dendritic cells from radioresistant precursors represents about 5.5-16% of the starting number of monocytes.

Physiologic counterparts for the maturation over several days of dendritic cells from nonproliferating blood progenitors can be proposed in at least three settings. First sizable numbers of dendritic cells traffic in afferent lymphatics, and these cells derive from precursors that have been proliferating 3-7 days prior to detection in lymph (Mason et al. 1981; Pugh et al. 1983; Fossum, 1989a; Fossum, 1989b). These afferent lymph dendritic cells may derive from blood progenitor cells that undergo a priming phase. Second, dendritic cells are rapidly induced to migrate into tissues [lung, gut] in response to pro-inflammatory stimuli e.g. LPS or infection (Watson et al. 1990; McWilliam et al. 1994). There they may undergo further maturation in response to cytokines that are produced locally by tissue macrophages.

Third, significant numbers of mature dendritic cells accumulate in rheumatoid synovial exudates during acute flares of arthritis (Zvaifler et al. 1985; Bhardwaj et al. 1988; Helfgott et al. 1988; Thomas et al. 1994). These effusions are rich in GM-CSF, IL-4, IL-6 and TNF alpha, amongst other cytokines [reviewed in (Klareskog et al. 1995)]. In addition, the presence of substantial numbers of macrophages and immune complexes may provide a natural "conditioned medium" for the maturation and differentiation of dendritic cells from blood progenitors that enter inflamed joints.

Based on the data reported in Examples 1 and 2, dendritic cells cultured from peripheral blood precursors in GM-CSF and IL-4 for 6-7 days can be considered as immature dendritic cells. Although they have already acquired relatively high levels of MHC and adhesion/costimulator molecules as well as the capacity to stimulate resting T cells they still lack markers for terminal dendritic cell differentiation such as CD83. They are however well equipped with the necessary prerequisites for the processing of native protein antigens. They can phagocytose particulate matter and they can efficiently process native tetanus toxoid protein into immunogenic MHC-peptide complexes recognized by a tetanus peptide-specific T clone. In addition, Sallusto et al. (1995) described active uptake of soluble macromolecules by macropinocytosis, and we find uptake of latex particles as well. Immature dendritic cells may therefore be useful in immunization protocols that use native proteins or particles as antigens. One must keep in mind, however, that the immature dendritic cells generated with GM-CSF and IL-4, but without CM, are not stable. Upon withdrawal of cytokines they re-adhere and appear to revert back to monocytes. Such cells would therefore not be as useful for therapeutic approaches. It will be preferred to induce maturation of antigen-pulsed dendritic cells by the method described here, i.e., exposure to monocyte-conditioned media.

Dendritic cells grown in GM-CSF and IL-4 for 7 days and exposed to macrophage-conditioned media for another three days develop into mature dendritic cells. These cells have down-regulated their antigen uptake mechanisms and their processing capacity. CM-treated dendritic cells correspond morphologically, phenotypically and functionally to well defined populations of mature dendritic cells, e.g., cultured epidermal Langerhans cells (Romani et al. 1989b); Tenunissen et al. 1990), cutaneous dendritic cells obtained by emigration from skin explants (Pope et al. 1995; Lenz et al. 1993), or blood dendritic cells obtained by classical methods involving 36 hours of culture (Young and Steinman, 1988). They are specialized in the sensitization of naive, resting T cells. We show here that they can efficiently induce proliferation in allogeneic umbilical cord T cells which may be considered virgin T cells. We also demonstrate that these mature dendritic cells can be loaded with an antigenic peptide and induce antigen-specific cytotoxic T lymphocytes from populations of autologous PBMC or CD8+ T cells. In addition, mature dendritic cells in small numbers are able to elicit rapid and virus-specific CTL responses from quiescent autologous T cells. Mature dendritic cells will be helpful in immunization protocols that employ antigenic peptides preferably to proteins. This applies especially to the field of tumor immunotherapy. Tumor-specific peptides are being discovered at a fast rate (Boon et al. 1994).

Based on our data, the optimal method to generate mature dendritic cells for clinical purposes would be to deplete PBMC of lymphocytes with immunomagnetic beads, culture them for 6 to 7 days in RPMI medium supplemented with 1% autologous human plasma and GM-CSF/IL-4, and induce them to mature within another three days of culture by the addition of conditioned medium that is produced by PBMC adhering to Ig-coated Petri dishes. All these reagents are already approved [Anti-mouse Ig Dynabeads and mouse anti-T and B cell mAb's/Baxter; GM-CSF/Sandoz; IL-4/Schering-Plough; 1 g/Biochemie-Sandoz] or have been used in clinical studies [RPMI medium, Lymphoprep].

Our method to generate dendritic cells from progenitor cells in autologous plasma will be useful in several respects. First, the method is simple, reproducible and generates $1-3 \times 10^6$ dendritic cells from relatively small, 40-50 ml blood samples. Second, critical features of dendritic cells such as pathways of antigen presentation and T cell signalling can be studied in the absence of foreign FCS derived proteins. Third, one has ready access to cells that can be used as adjuvants to enhance protective immune responses in vivo. We find that dendritic cells generated by the method described here and pulsed with either influenza virus [live or heat inactivated] or immunodominant peptides [Table 6] induce virus-specific CD8+ killer cell responses in vitro.

Pulsing Dendritic Cells with Antigen

The mature dendritic cells prepared according to this invention are useful for activating T cells against specific antigens. Several antigens and methods for priming dendritic cells have been described and may be adapted for use in this invention. See, for example Engleman et al. International patent application PCT/US95/07461; Hsu et al., *Nature Med.* 2:52-58 (1996); and Steinman et al. International application PCT/US93/03141 which are all incorporated herein by reference. Antigens associated with fungal, bacterial, viral, tumor, or autoimmune (i.e., self antigens) diseases are useful for priming dendritic cells to activate T cells which aid in treating or preventing disease.

Where it is desirable for cells to take up antigen by phagocytosis, it is preferable to add antigen to the cultures of immature dendritic cells prior to addition of the dendritic cell maturation factor. Phagocytosis may be desirable when particulate antigens, or immune complexes are used. In most cases it is sufficient to expose antigen to the dendritic cells after they have attained the mature phenotype or while they are exposed to the dendritic cell maturation factor to attain the mature phenotype. This method is preferred when soluble peptide antigens are used.

For the purpose of priming cells typically approximately 1 to $5 \times 10^6$ cells are exposed to antigen at a concentration of between about 10 pM to about 10 μM, inclusive. More preferably about 1 μM antigen to about 3 million cells is used. The dendritic cells are cultured in the presence of the antigen for a sufficient time to allow for uptake and presentation. Typically uptake and processing can occur within 24 hours but longer (up to and including 4 days) or shorter (about 1-2 hours) periods may also be used.

For activating T cells in an individual between about $2 \times 10^5$ and $2 \times 10^9$ more preferably between about 1 million and 10 million mature dendritic cells should be administered to the individual. The dendritic cells should be administered in a physiologically compatible carrier which is nontoxic to the cells and the individual. Such a carrier may be the cell growth medium described above. The mature dendritic cells prepared according to this invention are particularly potent at activating T cells. For example, using prior methods of obtaining dendritic cells the ratio of dendritic cells to T cells necessary for strong T cell activation is about 1 dendritic cell to 30 T cells whereas the ratio according to this invention is about 1 to 1000. Thus, fewer dendritic cells are required. For activating T cells in vitro the ratio of dendritic cells to T cells is between about 1:10 and 1:1000. More preferably between 1:30 and 1:150. Between approximately $10^8$ and $10^9$ activated T cells are administered back to the individual to produce a response against an antigen.

Dendritic cells may be administered to an individual using standard methods including intravenous, intraperitoneal, subcutaneously, intradermally or intramuscularly. The homing ability of the dendritic cells facilitates their ability to find T cells and cause their activation.

The methods of this invention are particularly well suited for use against tumors from which tumor specific antigens are obtainable or which express a mutated protein. Preferably, the antigen is a molecule required by the tumor cells to be malignant, for example altered ras. Non-limiting examples of tumors for which tumor specific antigens have been identified include melanoma, B cell lymphoma, uterine or cervical cancer. An example of a melanoma antigen which could be considered for use to prime dendritic cells is the human melanoma specific antigen gp75 antigen (Vijayasardhi S. et al., *J. Exp. Med.*, 171:1375-1380 (1990). An example of an antigen useful for targeting cells against cervical cancer is papilloma virus. Tumor specific idiotypic protein derived from B cell lymphomas has been reported to prime dendritic cells which activate T cells against the tumor cells. Hsu et al. (1966), supra. In addition to tumor antigens, viruses may also be used to prime the dendritic cells. Viruses may also be used to cause dendritic cells to present viral antigens, or they may be engineered to express non-viral proteins which are then processed and presented by the dendritic cells. Non-limiting examples of viruses which may be used to prime dendritic cells include, but are not limited to, influenza, HIV, CMV, EBV, human papilloma virus, adenovirus, HBV, HCV and vaccinia. Isolated viral proteins, inactivated or attenuated virus may also be used. Non-limiting examples of bacterial or protozoan antigens include tetanus toxoid, BCG, malaria antigens and leishmania antigens. Specific antigens associated with autoimmune disease such as immune receptors may also be used to prime dendritic cells to be used to activate T cells against such antigens.

Method of Assaying for a Dendritic Cell Maturation Factor

This invention provides an assay useful for identifying the dendritic cell maturation factor present in a test substance such as monocyte conditioned medium. This assay is based on the ability of immature dendritic cells to mature and express a stable phenotype after having been contacted with a dendritic cell maturation factor. Thus, the assay comprises contacting a culture of immature dendritic cells with a test substance and detecting the maturation of the immature dendritic cells in response to the presence of the test substance. The immature dendritic cells for use in this assay are derived from a population of pluripotential cells, such as human PBMCs having the potential of expressing either macrophage or dendritic cell characteristics and which express characteristics of immature dendritic cells when cultured in a medium containing cytokines (e.g., GM-CSF and IL-4). Maturation associated with the presence of a dendritic cell maturation factor may be confirmed, for example, by detecting either one or more of 1) an increase expression of one or more of p55, CD83, CD40 or CD86 antigens; 2) loss of CD115, CD14, CD32 or CD68 antigen; or 3) reversion to a macrophage phenotype characterized by increased adhesion and loss of veils following the removal of cytokines which promote maturation of PBMCs to the immature dendritic cells. The assay described above may be used in conjunction with biochemical techniques to identify the dendritic maturation factor present in monocyte CM. In addition, it provides a useful bioassay to confirm the activity of such a factor once it is identified or purified in connection with its manufacture.

EXAMPLES

Example 1

Methods

Culture Medium

RPMI 1640 supplemented with 20 μg/ml of gentamicin, 10 mM HEPES, and either 10% heat-inactivated FCS [Gemini Bioproducts, Calabasas, Calif.] or 1% and 10% autologous plasma [heparinized].

Cytokines

We were generously supplied with rhGM-CSF [$1 \times 10^5$ U/μg] by Kirin Brewery Co., Maebashi, Gunma, Japan, and rhIL-4 [$0.5 \times 10^5$ U/μg] by Immunex Corp. rhIL-12 [$2 \times 10^7$ U/mg] was provided by the Genetics Institute, Boston, Mass. The recombinant human cytokines IL-15, IL-1, IL-6, TNF alpha were purchased from R and D Corp [Minneapolis, Minn.].

Generation of Dendritic Cells from Human Blood

Peripheral blood was obtained from normal donors in heparinized syringes, and PBMC isolated by sedimentation in Ficoll-Hypaque [Pharmacia Biotech, Uppsala, Sweden]. T cell-enriched [ER+] and T cell-depleted [ER−] populations were prepared by rosetting with neuramimidase treated-sheep red blood cells as described (Carr and Kim, 1993). Different starting populations of PBMC were plated in 3 ml volumes in 6 well tissue culture dishes [Falcon] in complete medium. They consisted of [a] plastic adherent and nonadherent PBMC [obtained after 60 min adherence of $6 \times 10^6$ PBMC/well]; [b] ER− cells; [c] ER− cells sorted on a FACStar$^{Plus}$ into CD14 high or low cells. Groups [b]-[c] were plated at $2 \times 10^6$/well. GM-CSF and IL-4 were added at final concentrations of 1000 U/ml on the initial day of culture. Cytokines were replenished every other day [days 2, 4 and 6] by removing 0.3 ml of the medium and adding back 0.5 ml fresh medium with cytokines. On day 7, non-adherent cells were collected by moderately vigorous aspiration and analyzed immediately, maintained in culture or transferred to new 6 well plates. When cultured beyond 7 days, the cultures were supplemented with Pansorbin, [1:10,000 dilution of 2 mg IgG/ml, Calbiochem, La Jolla, Calif.], or conditioned medium [final concentration 33 or 50% v/v, see below] at day 7.

Conditioned Medium

Ig coated bacteriologic plates [100 mm, Falcon, Lincoln Park, N.J.] were prepared immediately prior to use by the addition of 4 ml of human gamma-globulin [10 mg/ml, Cappel Labs, Organon Teknika, Westchester, Pa.] for 1 min. The residual gamma-globulin was removed and saved for reuse at least 4-6 times. The plates were washed three times with phosphate buffered saline [PD] prior to use. T cell-depleted ER− cells [$5 \times 10^7$] were layered onto the Ig-coated bacteriologic plates for 1 hour in volumes of 6-8 ml. Non-adherent cells were washed off with gentle aspiration. The gamma-globulin adherent cells were incubated in fresh complete medium with 1% autologous plasma at 37° C. for 24 h. The medium was collected and frozen at −20° C. prior to use. In some cases, conditioned medium was prepared from cells stimulated with pansorbin instead of human Ig.

Monoclonal Antibodies [mAbs]

MAbs towards the following antigens were used: HLA-DR, CD14, CD3, CD4/CD8, CD5, CD19, CD16, CD56, CD1a, CD54, CD58, CD25, CD45RO, CD11a, CD11b and CD11c, [Becton-Dickinson, Mountainview, Calif.], CD80 and CD86 [IgG1, FITC conjugate, Pharmingen], CD83 [IgG1, PE conjugate, Coulter Corp, Miami, Fla.], CD68 [Dako, Carpinteria, Calif.], CD40, CD95/fas [Immunotech, Marseilles, France], p55 [K-2 clone, a gift from Dr. E. Langhoff; Mosialos et al. (1996)], mannose receptor [mAb 3.2PB1, a gift from Dr. A. Lanzavecchia], Lag anti-Birbeck granule associated antigen [a gift from Dr. S. Imamura], Ki 67 [MIB-1, IgG1, Dako]. Secondary antibody was PE-conjugated F[ab']2 goat anti-mouse IgG [gamma and light chain, Tago, Burlingame, Calif.].

Polyclonal Neutralizing Antibodies

Goat anti-human polyclonal antibodies were purchased from R and D Corp, Minneapolis, Minn. They included antibodies toward TNFa, IL-1 beta, IL-1 alpha, IL-12 and IL-6. Control antibody was goat IgG [R and D Corp.].

Cytofluorography and Cell Sorting

Cell populations were phenotyped with the panel of Mabs listed above and analyzed on a FACScan. To obtain CD14+ cells, $2 \times 10^7$ ER− cells were stained with PE-CD14 [Becton-Dickinson, Mountainview, Calif.] for 30 min on ice, washed extensively and then sorted on a FACStar$^{Plus}$. Both CD14 high and CD14 low cells were evaluated for the ability to develop into dendritic cells.

Immunohistochemistry

Cytospins of various cell populations were prepared using a Cytospin 2 centrifuge [Shandon, Inc., Pittsburgh, Pa.]. Slides were fixed in absolute acetone for 5 min at room temperature and then incubated with mAbs for 45 min. Cytospins were then washed and incubated with 1:200 dilution of biotinylated goat anti-mouse IgG [Boehringer Mannheim Biochemicals, Indianapolis, Ind.] for 45 min, followed by a horseradish peroxidase [HRP]-biotin-avidin complex [ABC kit; Vector laboratories, Inc., Burlingame, Calif.] for 30 min. Non-bound HRP was then washed off, and the HRP reaction product was developed with $H_2O_2$ and diaminobenzidine tetrahydrochloride [Polysciences, Warrington, Pa.].

Allogeneic MLR

To test for T cell stimulatory function, the APCs were unirradiated or irradiated [Gy 30] and added in graded doses as stimulators for $2 \times 10^5$ purified, allogeneic T cells in 96 well flat bottomed plates [Costar]. Proliferation was determined on days 4-6 with the addition of 4 μCi/ml of [$^3$H]TdR for 10-16 h to triplicate wells [mean cpm].

Induction of Influenza Virus Specific CTL

Dendritic cells prepared from HLA A2.1+ donors were washed out of medium containing serum and resuspended in RPMI to $0.5$-$1 \times 10^7$ cells/ml. Live or heat-inactivated influenza virus [PR8, Spafas Inc., Storrs, Conn.] was added at a final concentration of 1,000 HAU/ml for 1 hr at 37° as previously described (Bhardwaj et al. 1994; Bender et al. 1995) Following three washes, $3 \times 10^4$ dendritic cells were added to purified T cells [$1 \times 10^6$] in 48 well plates [Costar, Cambridge, Mass.] After 7 days, the T cells were assayed for cytolytic activity on uninfected or influenza-infected autologous macrophage targets using a conventional $^{51}$Cr release assay (Bhardwaj et al. 1994). Alternatively, targets were HLA A2.1 matched T2 cells [the TAP deficient line, provided by Dr. P. Cresswell] pulsed for 1 hr with 10 nM influenza matrix peptide [GILGFVFTL, SEQ ID NO:1]. Target cells were labeled with Na$^{51}$CrO$_4$ as previously described (Bhardwaj et al. 1994)

Results

Cells Cultured in the presence of GM-CSF and IL-4 only were not fully mature. We first confirmed that GM-CSF and IL-4 induces the development of large numbers of potent APCs from lymphocyte-depleted PBMC when cultured for 6-7 days in the presence of FCS [$2.5 \times 10^6$ per 40 ml of blood, Table 1 first row].

TABLE 1

Allogeneic MLR

| | $^3$H-TdR Incorporation, cpm × $10^{-3}$ AT T:APC ratios of: | | | | |
|---|---|---|---|---|---|
| Treatment | 100:1 | 300:1 | 900:1 | DC Yield/40 ml blood | % Enrichment |
| 10% FCS | 153 [17] | 33 [3] | 7 | 2.5 × 106 | 6% |
| 10% FCS + PS | 254 [196] | 154 [135] | 79 | 3.5 × $10^6$ | 95% |
| 10% FCS + CM | 258 [55] | 129 [27] | 39 | 3.8 × $10^6$ | 96% |
| 1% Plasma | 175 [3] | 68 [1] | 8 | 0.5 × $10^6$ | 25% |
| 1% Plasma + PS | 309 [154] | 161 [80] | 56 | 2.0 × $10^6$ | 75% |
| 1% Plasma + CM | 286 [8] | 156 [1] | 48 | 1.5 × $10^6$ | 74% |

Table 1: T Cell Stimulatory Activity of Dendritic Cells Derived from Progenitors in Blood ER− cells were cultured for 7 days in RPMI medium containing GM-CSF and IL-4 and either 10% FCS or 1% human plasma. The cells were then cultured for 4 more days in the absence or presence of conditioned medium prepared from pansorbin or gamma globulin stimulated blood mononuclear cells [50% final concentration]. T cell stimulatory MLR. Results are shown as $^3$H-TdR incorporation [cpm×$10^{-3}$] and are averages of triplicates. * Numbers in parentheses represent cpm measured with syngeneic T cells. The yield is expressed as the total number of dendritic cells obtained from an original donation of 40 ml of blood. The % enrichment is defined as the percentage of cells in the non-adherent fraction that display typical features of dendritic cells: stellate shape, high expression of HLA-DR, the dendritic cell restricted marker CD83 [see FIG. 2].

We discovered, however, that dendritic cells primed under these conditions were not fully mature. Upon immunolabeling of cytospins or cell suspensions [FACS], there was residual expression of the monocyte markers CD14 and CD32 and weak to no expression of the dendritic cell restricted markers CD83 (Zhou et al. 1992; Zhou and Tedder, 1995) and p55 (Mosialos et al. 1996).

Furthermore, when FCS primed cells were recultured without cytokines, MLR stimulating activity decreased considerably and most of the cells attached firmly to plastic [data not shown]. These findings suggested to us that GM-CSF and IL-4 were insufficient triggers to generate mature and stable dendritic cells from nonproliferating blood progenitors.

When 10% human serum or plasma was used in the GM-CSF/IL-4 priming culture in the place of FCS, most of the PBMC remained adherent and few free dendritic cells developed by 7 days. To reduce adherence, medium containing 1% plasma or serum was tested instead. Some small floating aggregates gradually developed over 4 days, and at day 7, some dendritic cells were evident. Although these cells exhibited potent T cell stimulatory capacity in the allo MLR, [Table 1, fourth row], the yield of dendritic cells was low, only $0.5 \times 10^6$ cells per 40 ml of blood. As with FCS, the cells exhibited variable CD14 and CD32 expression and failed to express CD83 and p55. Thus human plasma was even less efficient than FCS in priming for mature dendritic cell development.

Requirement for Conditioned Medium

Two approaches were tested to increase dendritic cell yield and maturity in FCS and human plasma. A 1:10,000 dilution of Pansorbin was added to the cultures after 7 days of growth in GM-CSF and IL-4, and the cells were recultured for 3-4 days. Pansorbin increased the number of free floating dendritic cells as well as T cell stimulatory capacity in the allo MLR [Table 1, second and fifth rows]. However, there was a dramatic stimulation of syngeneic T cells possibly because of superantigens in the pansorbin.

In the second approach, we used conditioned medium [CM] derived from supernatants of T-depleted mononuclear cells that had been adhered to gamma globulin-coated plates or stimulated with pansorbin [see Methods]. On day 7 of culture, one half of the medium was replaced with this CM. At day 11, 4 days after the addition of CM, both the yield and enrichment of dendritic cells increased. [Table 1, rows 3 and 6]. There was also significant enhancement of allo stimulatory capacity, but without the increase in the syngeneic MLR seen with pansorbin. Thus we chose to use CM and 1% human plasma for all subsequent experiments. Plasma is preferable to use over serum since it is readily obtained during the Ficoll separation of blood.

In >15 experiments, the overall effect of adding CM to plasma containing medium was to increase dendritic cell yields 3-10 fold [range of $0.3-3 \times 10^6$ per 40 ml of blood] and enhance enrichment from 2-25% to 30-90%. The contaminating cells are primarily lymphocytes, B cells and residual T cells. CM generated cells were phenotypically and functionally stable in that they retained their dendritic cell features when cultured in the absence of cytokines [see below]. No substantial difference was noted whether 33% vs. 50% CM was used or whether the CM was replenished every 2 days.

Figure 1:
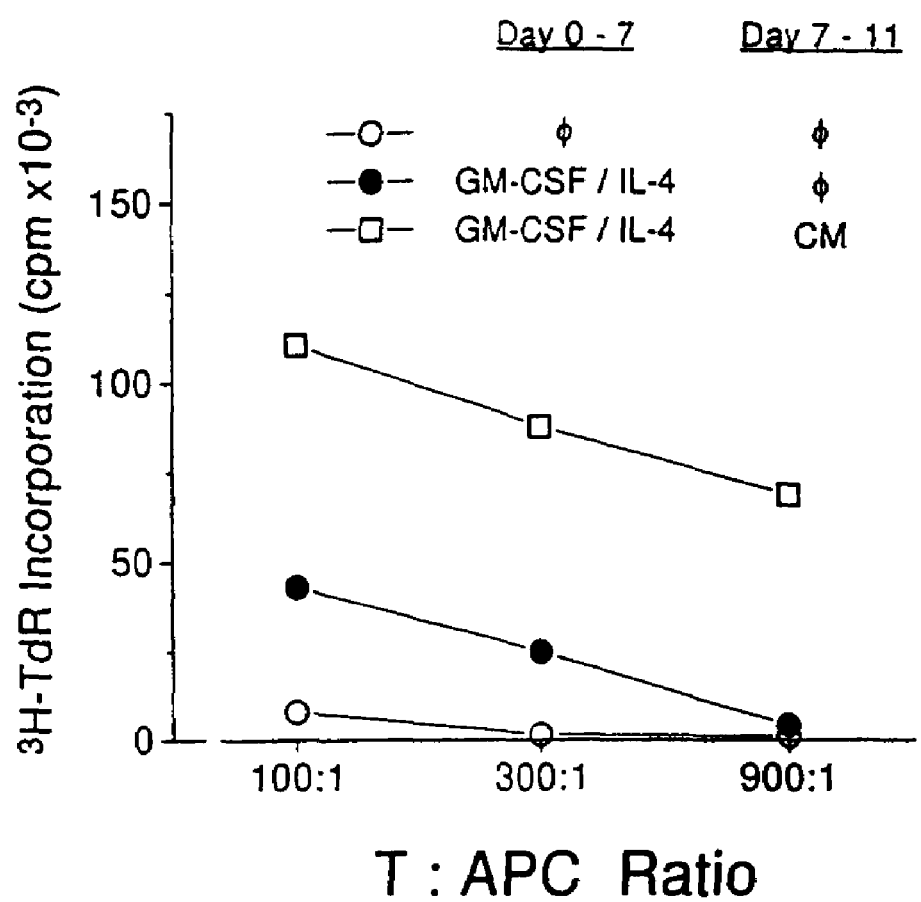
FIG. 1: Conditioned medium (CM) is required to ensure the maturation of dendritic cells from progenitor cells. ER– cells were cultured for 7 days in RPMI medium containing 1% plasma in the presence of GM-CSF and IL-4. Cells were then transferred to fresh plates and cultured for 4 days in the presence [open squares] or absence [closed circles] of CM. Control cultures were ER– cells cultured in Teflon beakers for 11 days [open circles]. T cell stimulatory function [primary allogeneic MLR] of the various APC populations is shown.

Throughout the above cultures, we noted the presence of residual adherent cells, most likely macrophages, in both components of the culture, i.e., during priming for 6-7 d with GM-CSF and IL-4, and during maturation for 3-4 d with CM. We therefore modified the protocol further. At day 7 of cytokine treatment, we directly transferred the nonadherent cells to fresh plates. We then cultured the cells for 4 additional days [day 11] in the absence or presence of CM. As expected, GM-CSF/IL-4 primed cells that were cultured without CM were suboptimal stimulators in the MLR [FIG. 1, closed circles]. In contrast, there was a substantial increase in stimulatory activity when cells received CM, [open squares]. ER– cells that were cultured in Teflon beakers without exogenous cytokines throughout the 11 days were poor APCs [open circles].

Figure 2B:
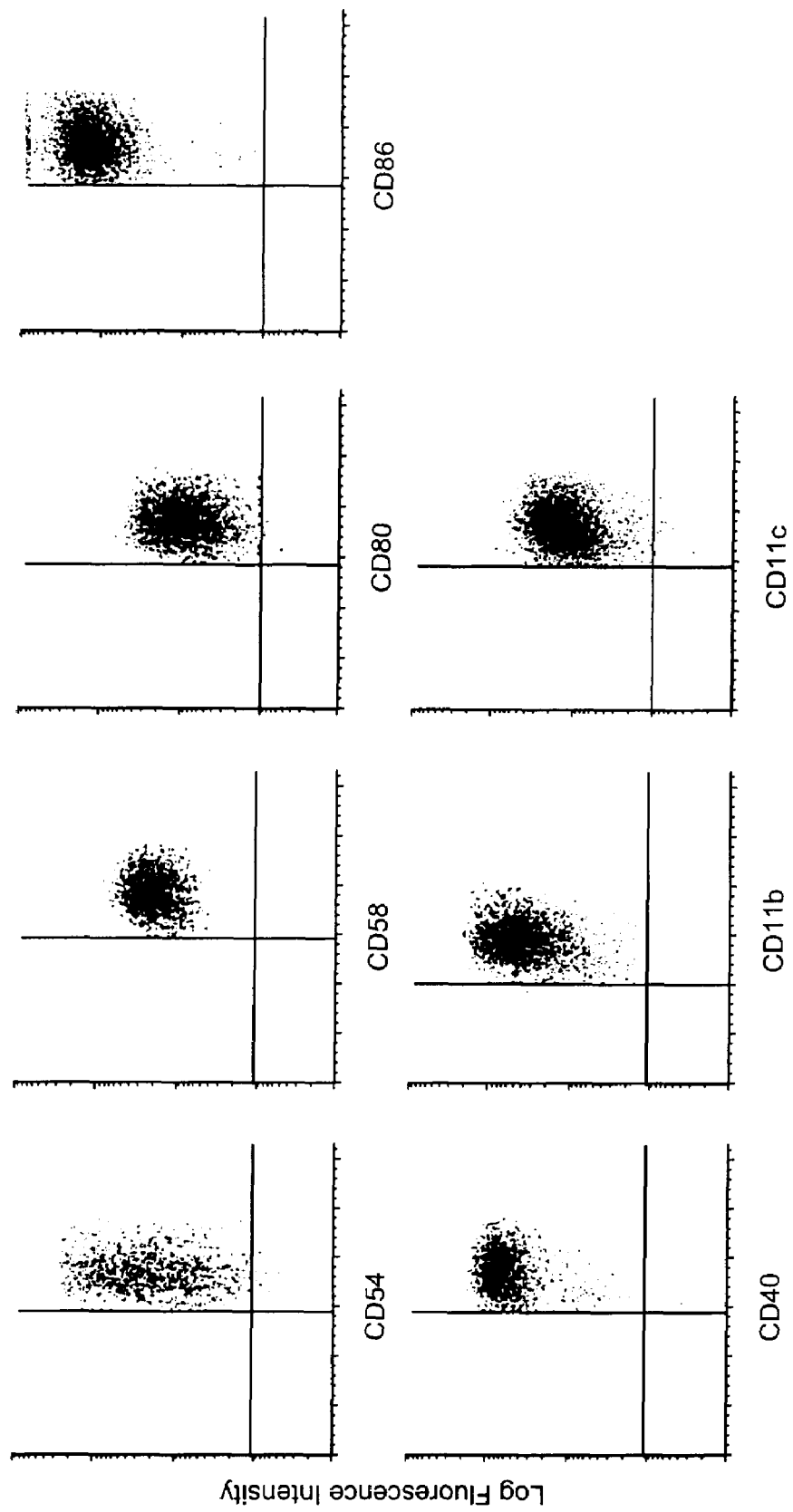
FIG. 2: Cytofluorographic analysis of dendritic cells grown in the presence of GM-CSF/IL-4 and CM. Dead cells and contaminating lymphocytes were excluded by light scatter properties. Dot plots of the remaining cells are shown. Isotype controls are shown in the left panel.
Figure 2C:
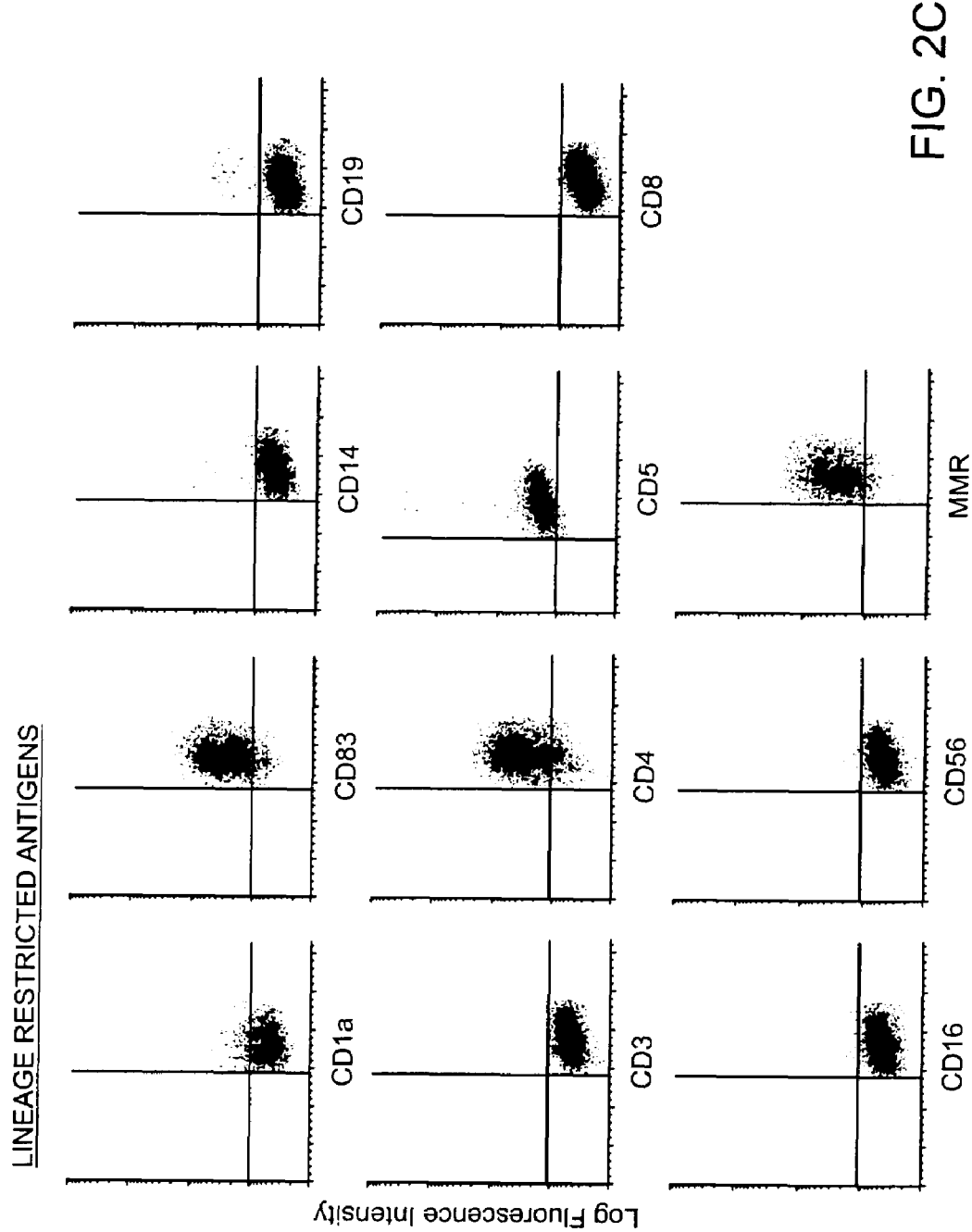
Figure 3:
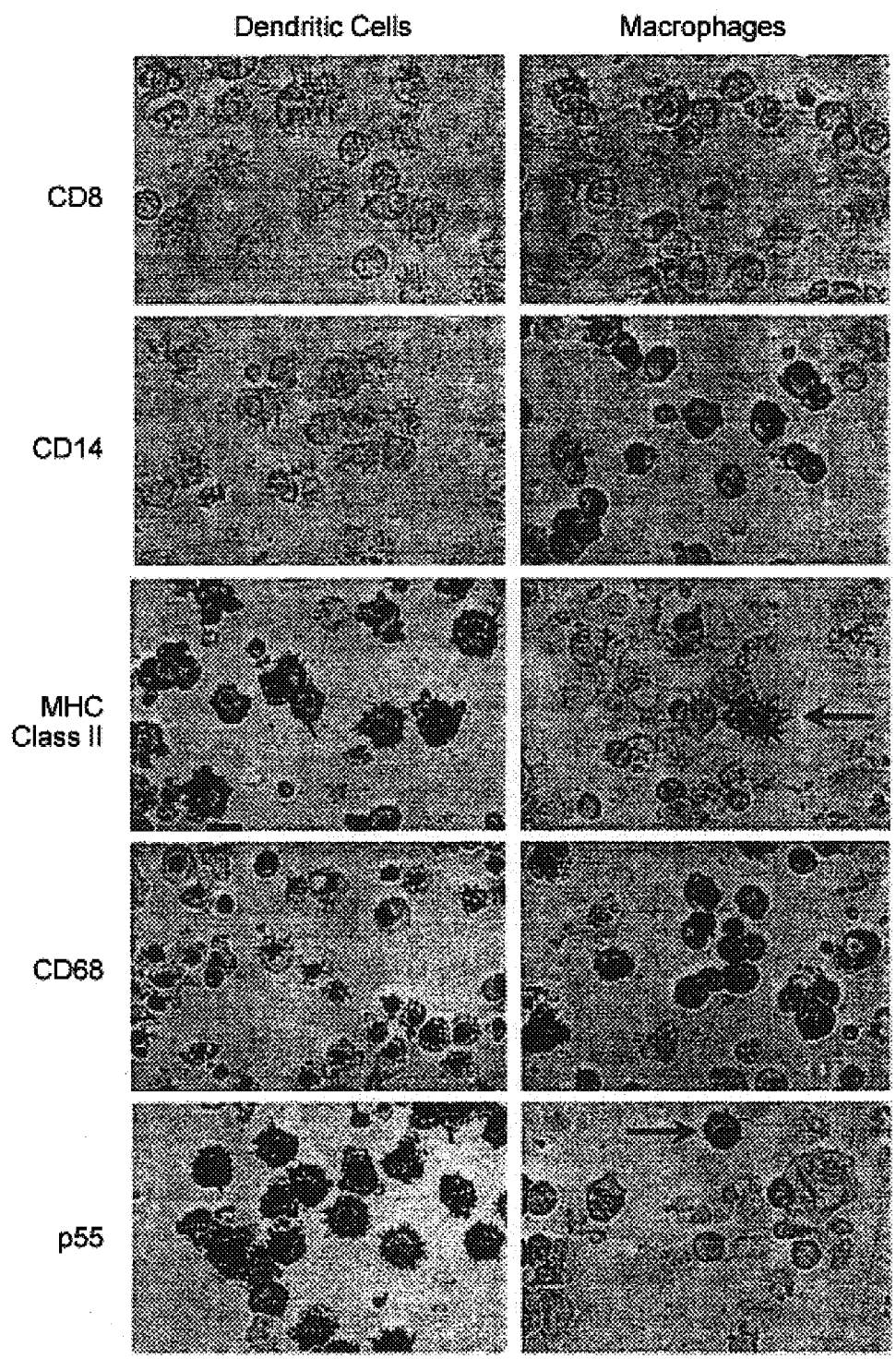
FIG. 3: Morphology and phenotype of blood derived dendritic cells and macrophages. Dendritic cells [left panel] were generated from normal blood ER– cells in the presence of GM-CSF/IL-4 and CM, cytospun onto glass slides and stained with a panel of mAbs [see Methods]. Macrophages were syngeneic ER– cells, enriched by plastic adherence and cultured for two weeks in Teflon beakers. CD8 serves as the isotype control antibody. Dendritic cells are distinguishable from macrophages by their dendritic shapes, lack of CD14 expression, high p55 expression and perinuclear pattern of CD68 expression. Black arrows in the right panel point to presumptive dendritic cells contaminating the macrophage populations.

Phenotypic Analysis of Dendritic Cells Grown from Normal Peripheral Blood with GM-CSF, IL-4 and Conditioned Medium The dendritic cells that were induced by this new culture procedure displayed a typical dendritic cell phenotype [FIG. 2] and morphology [FIG. 3]. The cells expressed high levels of MHC class II and accessory molecules for T cell stimulation [CD54, CD58, CD40, CD80, CD86]. The more lineage restricted antigens such as CD3, CD19, CD16, CD14 were absent. CD1a, CD4, CD11c and CD45RO were also expressed. CD68 or macrosialin (Ramprasad et al. 1995; Rabinowitz and Gordon, 1991), was expressed in a perinuclear pattern. This pattern is distinct from that seen with macrophages, where staining is seen throughout the cytoplasm. Only rare cells stained with the anti-Lag mAb that identifies Birbeck granules in epidermal dendritic cells.

Two new markers, CD83 and p55, recently have been shown to be selectively expressed by the small subset of mature dendritic cells in cultured human blood (Zhou et al. 1992; Zhou and Tedder, 1995; Mosialos et al. 1995). Both markers were expressed only at low levels by cells that are primed with GM-CSF and IL-4, but were unregulated following culture in CM. CD83 is a member of the Ig superfamily, and p55 is an EBV-inducible actin bundling protein in B cells (Zhou et al. 1992; Zhou and Tedder, 1995; Mosialos et al. 1995).

Stability of Dendritic Cells Generated in GM-CSF/IL-4 and CM

The stability of the dendritic cells generated at various points during the two step culture protocol described above was also ascertained. ER– cells were cultured with GM-CSF/IL-4 for 7 days and then analyzed for stimulatory activity in an allo MLR. Although these cells could stimulate allogeneic T cells [Table 2, first row], the phenotype was not typical of mature DCs [CD14+, moderate levels of HLA-DR, little to no CD83, and a diffuse staining for CD68; data not shown].

TABLE 2

| Treatment Culture supplements on days: | | | Day of MLR test | Allogeneic MLR $^3$H-TdR Incorporation (cpm × $10^{-3}$) at T:APC ratio of: | | |
|---|---|---|---|---|---|---|
| 0-7 | 7-11 | 11-14 | | 100:1 | 300:1 | 900:1 |
| GM + IL-4 | — | — | 7 | 161 | 145 | 81 |
| " | no CM | — | 11 | 203 | 146 | 25 |
| " | +CM | — | 11 | 154 | 172 | 161 |
| " | +CM | no CM | 14 | 144 | 170 | 189 |
| " | +CM | +CM | 14 | 178 | 207 | 165 |

Table 2: CM is Required for Optimal and Stable Immunostimulatory Activity

ER– cells were cultured in GM/CSF and IL-4 for 7 days, washed and then analyzed immediately for stimulatory activity in an allo MLR [first row], or cultured for 4 more days in the absence or presence of CM [second and third rows]. At day 11, aliquots of dendritic cells were maintained in CM for three more days [row 4] or washed extensively and recultured in the absence of CM [row 5]. The same donor of allogeneic T wells was used throughout these experiments. Results are shown as $^3$H-TdR incorporation [cpm×$10^{-3}$] and are averages of triplicates.

Cells washed out of cytokines at day 7 and recultured for 4 more days in the absence of CM had a similar phenotype and a noticeable decline in T cell stimulatory function when compared with dendritic cells grown in GM-CSF/IL-4 and CM [compare rows 2 and 3, Table 2]. Cells were next washed out of CM at day 11 and cultured for three more days [day 14] alongside cells that were left in CM. The dendritic cells were identical with respect to their phenotype and stimulatory capacity in the allogeneic MLR [rows 4 and 5, Table 2]. Thus, the exposure to CM renders an apparent irreversible change that leads to functionally mature dendritic cells.

Attempts to Identify the Active Cytokines in CM

Figure 4:
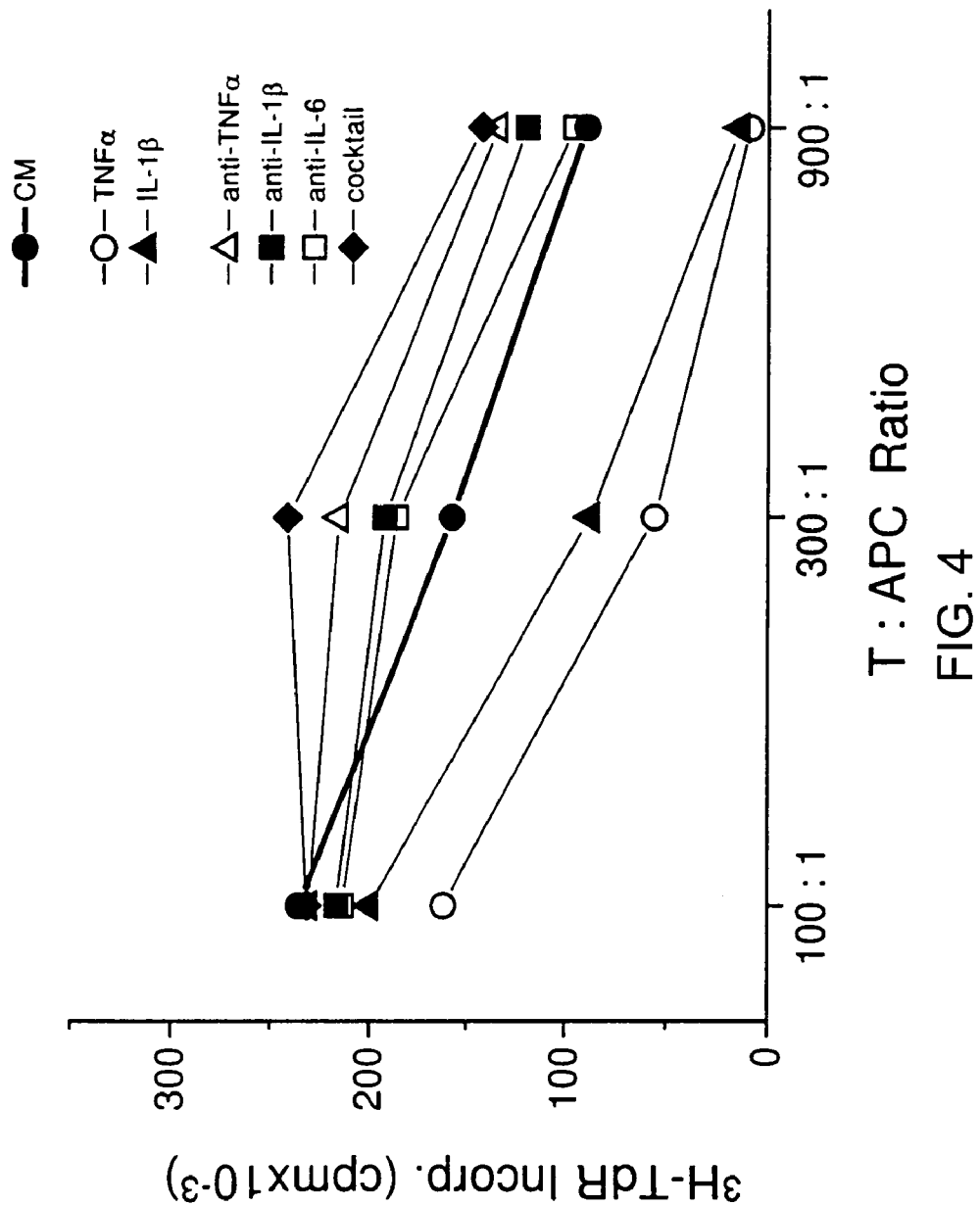
FIG. 4: Attempts to replace conditioned medium with cytokines. ER– cells were cultured in GM-CSF/IL-4 for 7 days and then transferred to fresh tissue culture plates. The cells were supplemented with 50% CM [black circles] in the absence or presence of polyclonal neutralizing antibodies to TNFα, IL-1β and IL-6 [1-5 μg/ml]. Cocktail refers to the combination of the various antibodies. Some cultures received TNF alpha [20 ng/ml] or IL-1 beta [10 ng/ml] instead of CM. After 4 days [day 11 of culture], the cells were evaluated for T cell stimulatory activity in an allo MLR. Results are shown as $^3$H-TdR incorporation [cpm×$10^{-3}$] and are averages of triplicates.

The CM from blood cells that are cultured in human gamma globulin likely contain many monocyte-derived cytokines such as IL-1, IL-6 and TNFα. However, none of these cytokines could replace the CM, and in fact each cytokine had no effect on increasing dendritic cell yield or function [FIG. 4 and Table 3]. The cytokines IL-12 and IL-15 were also ineffective [Table 3].

TABLE 3

| Treatment Culture supplements on day 7 | | Allogeneic MLR $^3$H-TdR Incorporation (cpm × $10^{-3}$) at T:APC ratio of: | | |
|---|---|---|---|---|
| CM | Other | 100:1 | 300:1 | 900:1 |
| + | goat IgG [4 µg/ml] | 147 | 117 | 46 |
| + | goat IgG [17 µg/ml] | 141 | 94 | 31 |
| + | α TNF-α [1 µ/ml] | 144 | 120 | 61 |
| + | α IL-6 [4 µg/ml] | 161 | 120 | 31 |
| + | α IL-12 " | 180 | 104 | 43 |
| + | α IL-1-α " | 152 | 90 | 33 |
| + | α IL-1-β " | 163 | 112 | 37 |
| + | cocktail [17 µg/ml] | 116 | 59 | 19 |
| — | TNF-α [10 ng/ml] | 79 | 38 | 11 |
| — | IL-1-β " | 72 | 47 | 4 |
| — | IL-12 [500 ng/ml] | 55 | 21 | 4 |
| — | IL-15 " | 46 | 12 | 4 |

Table 3: Attempts to Identify the Factors in CM that Promote Dendritic Cell Differentiation ER– cells were cultured in GM/CSF and IL-4 for 7 days, and then supplemented with CM for 4 days in the presence of neutralizing antibodies to a panel of cytokines. Goat IgG was the control. Cocktail refers to the combination of the various antibodies. Some cultures were supplemented with recombinant cytokines alone in the absence of CM. At day 11 of culture the cells were evaluated for their ability to stimulate allogeneic T cells. Results are shown as $^3$H-TdR incorporation [cpm×$10^{-3}$] and are averages of triplicates.

We also added polyclonal neutralizing antibodies to cytokines to the CM. However, antibodies to TNFα, IL-1, and IL-6 did not block the capacity of CM to increase dendritic cell yields and function [FIG. 4 and Table 3].

Source of DC progenitors in PBMC

The progenitor cells that give rise to dendritic cells produced according to an embodiment of the invention [GM-CSF+IL-4 followed by CM] where characterized. To assess the adherence of progenitors to plastic, ER– cells were adhered for 1 hour in 6 well plastic plates [2×$10^6$ per well] after which nonadherent cells were removed and replated in new dishes. Both populations were cultured in GM-CSF and IL-4 for 7 days followed by CM for 4 days. Adherent ER– cells yielded the highest number and purity of dendritic cells [Table 4]

TABLE 4

| DC progenitors are present in both adherent and non-adherent ER - fractions. | | | | | |
|---|---|---|---|---|---|
| Cell population | DC Yield/ 40 ml blood | % Enrichment | Allogeneic MLR $^3$H-TdR incorporation (cpm × $10^{-3}$) at T:APC ratio of: | | |
| | | | 100:1 | 300:1 | 900:1 |
| ER - | 0.8-1.5 × $10^6$ | 79-90 | 265 | 243 | 169 |
| ER -, adherent | 1.3-2.8 × $10^6$ | 94-96 | 226 | 222 | 147 |
| ER -, non-adherent | 0.8-1.7 × $10^5$ | 27-36 | 219 | 192 | 73 |

Table 4: Dendritic Cell Progenitors are Present in both Adherent and Nonadherent ER– Fractions ER– cells were adhered to plastic for 1 hr. Both adherent and nonadherent cells were collected and cultured with GM-CSF and IL-4 for 7 days, followed by CM. At day 11, the yield and % enrichment of dendritic cells was determined. The T cell stimulatory function of the ER– populations analyzed is also shown. Results are representative of 2 experiments and were similar to cells derived from bulk ER– cells in terms of immunostimulatory capacity. ER– nonadherent cells also generated some potent APCs, but the yield and purity of dendritic cells was substantially less, primarily because of a large number of contaminating lymphocytes. Thus progenitors appear to reside in both adherent and nonadherent populations of blood mononuclear cells.

Figure 5A:
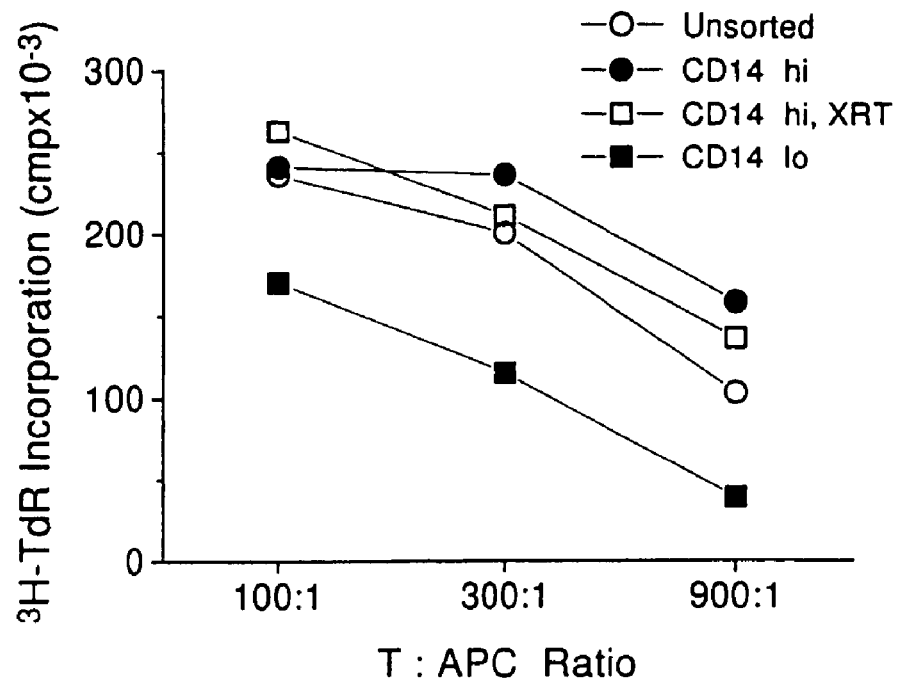
FIG. 5: Dendritic cell progenitors are enriched in the CD14 hi population. ER– cells from two different sources were sorted into CD14 hi and lo populations as described in Methods. Unsorted and various sorted fractions were analyzed for T cell stimulatory activity in an MLR. In [A], the CD14 hi cells were irradiated with 3,000 rads, 137 Cs source. In [B], the CD14 hi cells were irradiated with 1,500 rads. Results are shown as $^3$HTdR incorporation [cpm×$10^{-3}$] and are averages of triplicates.
Figure 5B:
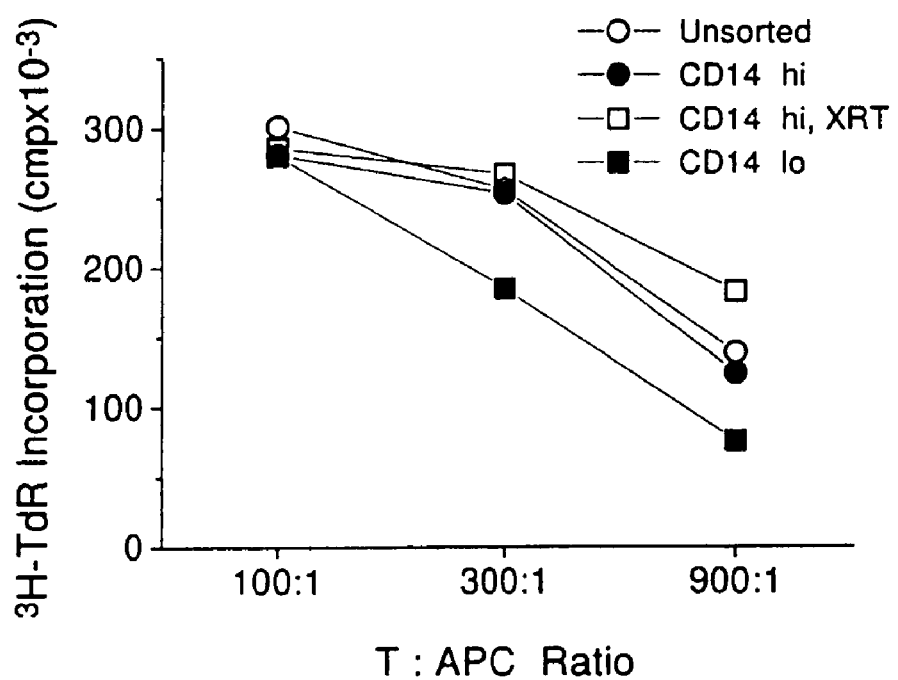

ER- cells were stained with PE-conjugated anti-CD14 and the cells were sorted in a FACStar into CD14 high and CD14 low fractions. Negative small cells were excluded by gating. These were then cultured for 7 days with GM-CSF and IL-4 followed by 4 days in CM. CD14 high cells were also evaluated with or without prior treatment with ionizing irradiation [Gy 15 or 30]. The greatest yield, percent enrichment and T cell stimulatory activity were found in the unirradiated CD14 high population [Table 5 and FIG. 5].

TABLE 5

| DC progenitors are enriched in the CD14 hi population | | |
|---|---|---|
| Cell population | Yield/40 ml blood | % Enrichment |
| CD14 hi | 1.2-2 × $10^6$ | 66-97 |
| CD14 lo | 0.7-0.8 × $10^6$ | 10-39 |
| CDF14 hi, XRT | 1-1.6 × $10^6$ | 72-77 |
| CD14 hi + lo | 1-1.3 × $10^6$ | 57-73 |

[n = 2]

Table 5: Dendritic Cell Progenitors are Enriched in the CD14 hi Population

ER– cells were stained with CD14-FITC and sorted into CD14 hi and dim populations. Separated fractions, irradiated CD14 hi cells [Gy 15 and 30] and stained unsorted or combined cells [CD14 high+low] were cultured with GM-CSF/IL-4 followed by CM. The yields and % enrichment of dendritic cells is shown.

Interestingly, irradiated CD14+ high cells generated effective dendritic cells but the yield was 50% lower, and the percent enrichment was slightly lower, 77% vs. 97% for nonirradiated CD14+ cells. The CD14 low fraction also produced some typical dendritic cells, but the yield and enrichment were significantly lower than the CD14 high population, probably because there is a significant number of lymphocytes contaminating this fraction.

Collectively, our data suggest that dendritic cell progenitors are found in PBMC populations that are both plastic adherent and nonadherent, as well as CD14 dim and CD14 high. Furthermore, some of these progenitors are radioresistant.

Dendritic Cells Derived from Non-Proliferating Progenitors Induce Strong Anti-Viral Cytolytic T Cell Responses Potent human CD8+ cytolytic T cell [CTL] responses to live replicating influenza A virus are generated when dendritic cells are the APCs (Bhardwaj et al. 1994). When pulsed with poorly replicating, heat-inactivated, influenza virus, dendritic cells induce equally strong CTL responses (Bender et al. 1995). Other APCs, e.g., macrophages lack this capacity. Since the heat inactivated virus is incapable of substantial new protein synthesis, only small amounts of viral protein are required to charge class I molecules on dendritic cells. Dendritic cells prepared as described above from non-proliferating progenitors in blood were tested for their capacity to elicit anti-viral CTL responses to live and heat-inactivated influenza virus [Table 6].

TABLE 6

|  | Percent specific lysis of targets | |
| --- | --- | --- |
| Infection of dendritic cells | Mo [−] | Mo [Flu] |
| [−] | 2.5 | 1.9 |
| Live Flu | 1.3 | 60.4 |
| Infection of dendritic cells | T2 [−] | T2 [Matrix peptide] |
| [−] | 0 | 10 |
| Heated Flu | 30 | 77 |

Table 6: Dendritic Cells Derived from Non-proliferating Progenitors Induce Strong Anti-viral Cytolytic T Cell Responses Dendritic cells were uninfected or infected with live replicating or heat inactivated influenza virus [see methods] and concultured with autologous HLA A2.1+ T cells [T:APC ratio=30:1].

After 7 days, T cells were harvested and tested for cytolytic activity on chromium labeled syngeneic macrophages [mos] which were infected or uninfected with influenza virus [upper panel]. Lytic activity of T cells responding to dendritic cells infected with heat inactivated influenza virus was tested on chromium labeled T2 target cells [lower panel] that had been pulsed with 10 nM of HLA A2.1 restricted matrix peptide. E/T ratio in both experiments was 30:1.

Both forms of virus could be presented to autologous T cells to induce CTL responses. CD8+ T cells are the likely mediators, since they efficiently lysed TAP deficient T2 cells pulsed with the HLA A2.1 restricted influenza matrix peptide.

Conditions for Generating Mature Dendritic Cells from Progenitors in Human Plasma The method of preparing mature dendritic cells according to this invention preferably uses two steps. Two steps are preferred because dendritic cells generated in either FCS or human plasma containing medium failed to develop and maintain a stable phenotype and function when removed from GM-CSF and IL-4. For example, these "putative" dendritic cells continued to express CD14 and CD32, which are typically absent from mature dendritic cells, expressed little or no CD83 and p55 and lost stimulatory function upon removal of GM-CSF/IL-4. This phenomenon has not been previously appreciated, since the cells are typically used without reculturing them in the absence of cytokines (Sallusto and Lanzavecchia, 1995; Sallusto and Lanzavecchia, 1994). Second, exposure to a dendritic cell maturation factor such as CM was an absolute requisite to induce the formation of large numbers of fully differentiated dendritic cells from the GM-CSF and IL-4 primed cultures. The CM-induced cells expressed a typical phenotype, with strong expression of a] antigen presenting MHC class I and II products and CD1a, b] several adhesions and co-stimulator molecules including CD40, CD54, CD58, CD80 and CD86, and c] two dendritic cell restricted molecules, CD83 and p55. This phenotype remained stable following removal of all growth factors. Moreover, the yield and T cell stimulating potency of the CM-treated cells were substantial. Up to $3 \times 10^6$ dendritic cells were obtained from 40 ml of blood, which is 3 times more than the number of mature dendritic cells that are present in one unit [500 ml] of non treated blood cells. The cells induced strong allo MLRs even at DC:T ratios of 1:900. It is preferred to first prime the blood progenitors with GM-CSF and IL-4 for 6-7 days before adding the CM, since the latter seems to be less effective if added at day 0 [data not shown].

Dendritic Cell Derived from Blood Progenitors Express a Unique Pattern of Antigens We find that CD83 and p55 are useful markers for the development of mature dendritic cells from blood progenitors. Both antigens are uniformly expressed at high levels in mature cells but are lacking in fresh blood monocytes and in progenitors that are primed in GM-CSF/IL-4 for 7 days but are not matured in CM. Another useful marker to distinguish dendritic cells from monocytes is CD68 [termed macrosialin in the mouse], a member of the lamp-1 family. This antigen is detected in a perinuclear area in dendritic cells, whereas much of the cytoplasm stains for CD68 in monocytes, as has been emphasized by Gordon and others (Rabinowitz and Gordon, 1991; Ramprasad et al. 1995).

Example 2

Materials And Methods

Culture Medium

The following culture media were used: RPMI 1640 [Biological Industries, Kibbutz Beit Haemek Israel]; X-VIVO10, 15, and 20™ [Bio-Whittaker, Walkersville, Md.]; Hybricare and AIM-V™ [GIBCO-BRL, Gaithersburg, Md.]. They were supplemented with 50 g/ml of gentamicin. Sources of serum were FCS [10%, Biological Industries or Seromed-Biochrom, Berlin, Germany], and human plasma and serum [0.5, 1, 5, and 10%] from either adults [PAA Laboratories GmbH, Lin, Austria, blood bank or autologous] or from umbilical cord blood [kindly provided by the Department of Gynecology and Obstetrics]. FSC and, in some experiments only, human sera/plasma was heat-inactivated at 56° C. for 30 minutes.

Cytokines and Anti-Cytokines

Recombinant human GM-CSF was generously provided by Dr. E. Liehi, Sandoz Ges.m.b.H., Vienna, Austria [specific activity $5.9 \times 10^6$ U/mg]. Alternatively, human GM-CSF prepared for therapeutical purposes was used [Leukomax™, Sandoz, Basel, Switzerland, specific activity $1.1 \times 10^7$ U/mg). Recombinant human IL-4 was a gift of Dr. M. B. Widmer, Inmmunex Corp., Seattle, Wash. (specific activity $5 \times 10^7$ U/mg] and Dr. E. Liehl, Sandoz, TNF-α was supplied by Dr. G. R. Adolf [Bender, Vienna, Austria; specific activity $6 \times 10^7$ U/mg]. IL-12 was provided by the Genetics Institute, Boston, Mass. [specific activity $3.6 \times 10^8$ U/mg]. Human IL-1β [specific activity $5 \times 10^8$ U/mg] and simian IL-15 [specific activity $1 \times 10^7$ U/mg] were purchased from Genzyme Corp., Cambridge, Mass. human stem cell factor [specific activity $0.5$-$1.0 \times 10^6$ U/mg] from R&D Systems [MO]. Human IL-15 and a neutralizing rabbit anti-human IL-15 antibody were from PeproTech, London, UK. Human IL-13 was a gift of Dr. A. Minty, Sanofi, Labege, France and was also obtained from Pharmingen, San Diego, Calif. [specific activity $1 \times 10^6$ U/mg].

Initial Processing of Human Blood

Peripheral blood was obtained from the local blood bank as standard buffy coat preparations and from normal donors. Preservative-free heparin [200 I.U./ml blood; Novo Nordisk A/S, Bagsvaerd, Denmar] was used to prevent clotting. PBMC were isolated by centrifugation in Lymphoprep [1.077 g/ml; Nycomed Pharma AS, Oslo, Norway]. In order to minimize contamination of PBMC with platelets the Lymphoprep centrifugation [200×g/room temperature] was interrupted after 20 minutes. The top 20-25 ml containing most of the platelets were carefully removed and centrifugation was resumed [20 minutes/460×g/room temperature]. PBMC were then depleted of T and B cells by means of an immunomagnetic technique. Dynaeads [Dynal, Oslo, Norway] M-450 Pan-B/CD 19 and M-450 Pan-T/CD2 were washed four times with PBS containing 1% bovine serum albumin or human plasma. PBMC [30-50×10$^6$/ml] were incubated with the magnetic beads at a ratio of 1:1:1 at 4° C. for 20 min. using Dynal mixer. Lymphocytes were then depleted by means of a Dynal magnet [1-2 minutes]. Magnet-non-adherent cells were harvested and washed. This depletion step was repeated once. In some experiments an indirect immunomagnetic approach was used. PBMC were labeled with anti-T and B cell mAb's [hybridoma supernatant of mAb OKT-11/CD2 and ascitic fluid of mAb MEM-97/CD20; gift of Dr. v. Horejsi, Praha, Czeck Republic], washed three times and incubated with sheep anti-mouse Ig-coupled magnetic beads [SAM-M450; Dynal] at a ratio of 3 beads to one cell. Magnetic separation was achieved as described above. In addition, lymphocyte-depleted PBMC were obtained from cancer patients [after informed consent] in complete remission during hematopoietic recovery after high-dose consolidation chemotherapy and subcutaneous daily administration of 300 μg G-CSF [Neupogen™, Hoffmann-La-Roche, Basel, Switzerland]. Depletion of PBMC from CD34+ cells was achieved either by means of M-450/CD34 magnetic beads [Dynal] or by passing cells through an immunoaffinity anti-CD34 column [CellPro Inc., Bothell, Wash.] that is clinically used for transplantation purposes. PBMC from normal donors treated with G-CSF in the same manner were also used. This study was approved by the Ethical Committee of the Medical Faculty, University of Innsbruck.

Culture Technique

Lymphocyte-depleted PBMC were planted in 6-well tissue culture plates at a density of $2 \times 10^6$ cells/well in 3 ml of complete culture medium. GM-CSF and IL-4 were added at final concentrations of 800 and 1000 U/ml, respectively. Cultures were fed every other day [days 2, 4 and 6] by removing 1 ml of the medium and adding back 1.5 ml fresh medium with cytokines [1600 U/ml GM-CSF and 1000 U/ml Il-4, resulting in final concentrations of 800 and 500 U/ml, respectively]. On day 7, non-adherent cells were either harvested and analyzed or transferred to new 6 well plates and cultured further in the presence or absence of maturation stimuli [see below]. GM-CSF and IL-4 were present during the culture period from day 7 to day 10-11.

Stimuli for Dendritic Cell Maturation

SACS [fixed *Staphylococcus aureus* Cowan 1 strain, 2.01 mg/ml Ig-binding capacity, Pansorbin cells, Cat No. 507861] was purchased from CalBiochem Co., La Jolla, Calif. It was added to dendritic cell cultures at a final dilution of 1:10000. Conditioned medium was produced by Ig-adherent PBMC. To this end, bacteriologic plates [100 mm. Cat. No. 1029, Falcon, Oxnard, Calif.] were incubated with a solution of human Ig [10 mg/ml, therapeutically used "Immunoglobulin i.v. Biochemie", Biochemie Ges.m.b.H., Vienna, Austria, subsidiary of Sandoz] in PBS for 1 minute at room temperature. After three rinses with PBS $5 \times 10^7$ PBMC were put into one Ig-coated bacteriologic plate for 1 hour at 37° C. in 8 ml of complete culture medium. Non-adherent cells were rinsed away and adherent cells were cultured in fresh complete medium at 37° C. for 24 h.

Complete media consisted of the different media and serum supplements mentioned above. Conditioned media were sterile filtered and stored at +4° C. for one week at the longest or frozen at −20° C. In some cases, conditioned medium was prepared from cells stimulated with SCS instead of human Ig. Conditioned media were routinely used at 25% vol/vol. Increasing this concentration up to 50% was not appreciably better.

Flow Cytometry and Immunohistochemistry

Primary antibodies used for flow cytometric and immunohistochemical analyses are listed in Table 7.

TABLE 7

Antibodies used for immunohistochemistry

| Specificity | Clone/Name | Ig class | Source | Reference |
|---|---|---|---|---|
| HLA-DR/DQ | 9.3F10/HB 180 | mouse IgG2a | ATCC[a] | |
| HLA-DR | L243/HB55 | mouse IgG2a | ATCC | |
| HLA-DR-FITC | L243 | mouse IgG2a | BDIS[b] | |
| CD1a | OKT-6/CLR8020 | mouse IgG1 | ATCC | |
| CD1a-FITC | OKT-6 | mouse IgG1 | Ortho[c] | |
| CD15s | CSLEX1 | mouse IgM | BDIS | |
| CD40 | G-28.5 | mouse IgG1 | E. A. Clark[d] | |
| CD44v9 | VFF16 | mouse IgG | P. Herrlich[e] | |
| CD45RA | 4G10 | mouse IgG2a | R. M. Steinman[f] | |
| CD45RO | UCHL10 | mouse IgG2a | DAKI[g] | |
| CD68 | EBM11 | mouse IgG1 | DAKO | |
| CD71 | RPN.511 | mouse IgG1 | Amersham[h] | |
| CD80 | L307.4 | mouse IgG1 | BDIS | |

TABLE 7-continued

Antibodies used for immunohistochemistry

| Specificity | Clone/Name | Ig class | Source | Reference |
|---|---|---|---|---|
| CD83 | HB-15a | mouse IgG2b | T.F. Tedder[i] | (Zhou et al. 1992) |
| CD86 | IT2.2 | mouse IgG2b | Pharmingen[j] | |
| CD115/c-fms CSF-1-receptor | Ab-1 (clone 2-4A5-4) Ab-2 (clone 3-4A4-E4) | rat IgG1 rat IgG2b | Oncogene Science[k] | Ashmun et al., 1989 |
| Birbeck granules | Lag | mouse IgG1 | S. Imamura[l] | (Kashihara et al. 1986) |
| Proliferation-associated | Ki-67 | mouse IgG1 | DAKO | |

[a]American Type Culture Collection, Rockville, MD;
[b]Becton-Dickinson Immunocytometry Systems, Mountain View, CA;
[c]Ortho, Raritan, MJ;
[d]Seattle, WA;
[e]Kernforschungszentrum, Karlsruhe, Germany;
[f]The Rockefeller University, New York, NY;
[g]Roskilde, Denmark;
[h]Amersham, UL;
[i]Duke University, Durham, NC;
[j]San Diego, CA;
[k]Cambridge, MA;
[l]Kyoto University, Kyoto, Japan Secondary antibody was biotinylated anti-mouse or anti-rat Ig's followed by FITC- or PE-conjugated streptavidin [Amersham International, Amersham, UK]. Dead cells were gated out on the basis of their florescence with propidium iodide or by their light scatter properties. Analyses were done on a FACScan instrument [Becton-Dickinson, Mountain View, Calif.]. Cytospins were prepared with Cytospin 2 centrifuge [Shandon, Inc., Pittsburgh, Pa.]. Slides were acetone-fixed for 5 min. at room temperature and then incubated with primary mAbs for 15 minutes followed by biotinylated sheep anti-mouse Ig [1:200; Amersham] and Texas Red-conjugated streptaviden [1:50, Amersham]. For double labeling purposes this staining sequence was extended with a blocking step [100 µg/ml mouse gamma globulin] and FITC-conjugated anti-HLA-DR [Becton-Dickinson]. Slides were mounted in Vectacshield™ [Vector Laboratories, Burlingame, Calif.]

Allogenic MLR and Processing/Presentation of Soluble Antigen

To test for T cell stimulatory function, the APCs were irradiated with 30 Gy from a Cs source and added in graded doses as simulators for $2 \times 10^5$ purified [nylon wool-non adherent; anti MHC class II-panned], allogeneic T cells in 96 well flat bottomed plates [Falcon]. For some experiments T cells were purified from umbilical cord blood in order to obtain naive T cells. Proliferation was determined on days 4-6 with the addition of 4 µCi-148 KBq/ml of [$^3$H]TdR [specific activity 247.9 GBq/mmol=6.7 Ci/mmol; New England Nuclear, Boston, Mass.] for 12-16 h to triplicate wells [mean cpm]. Processing and presentation of tetanus toxoid protein [Connaught, Willowdale, Ontario, Canada] was measured with a HLA-DP4-restricted tetanus-peptide-specific T cell clone [AS11.15] that was a gift of Dr. A. Lanzavecchia, Basel Switzerland (Lanzavecchia, 1985). Graded doses of irradiated dendritic cells were co-cultured with $1.5 \times 10^4$ clone cells in the presence or absence of tetanus toxoid [5 and 1 µg/ml]. [$^3$H] TdR was added from d2 to d3.

To generate cytotoxic T cells, the approach described by (De Bruijn et al. 1992) was used with modifications. Irradiated [12.5 Gy] dendritic cells as simulators were co-cultured with autologous PBMC or with CD8+ T lymphocytes [1:25] as responders in the presence of 100-200 µM peptide MP 58-66 of influenza matrix protein [MedProbe, Oslo, Norway] in 2 ml RPMI/10% human serum in wells of a 24-cell tissue culture plate. After one week the cultures were fed with 40% Lymphocult [Biotest, Dreieich, Germany]. The lytolytic potential of outgrowing T cells was assessed two to four weeks after the start of the cultures in a standard Chromium-release cytotoxicity assay using as target PHA-stimulated autologous T cell blasts, that had been incubated with different concentrations of the peptide. Results are expressed as % specific lysis. CD8+ T lymphocytes were prepared by indirect immunomagnetic depletion of CD4+ T cells using mAb VIT-4/anti-CD4 [gift of Dr. W. Knapp, Vienna, Austria] followed by sheep anti-mouse IgG magnetic beads [Dynal].

Additional Reagents

Latex beads [0.5% vol/vol; 2 µm diameter] for phagocytosis experiments were purchased from Seradyn, Indianapolis, Ind. They were added to the cell cultures at a final dilution of 1:20. Staphylococcal enterotoxin A [superantigen SEA] was from Sigma Chemical Corp. St. Louis, Mo. It was used at a final concentration of 25 µg/ml. LPS [Sigma] was added to some experiments at a final concentration of 100 ng/ml.

Results

Identification of Culture Conditions Allowing Full Maturation of Dendritic Cells Dendritic cells grown in GM-CSF and IL-4 are not fully mature. Lymphocytes were depleted from PBMC by means of immunomagnetic beads. Use of the immunomagnetic beads allowed for the omission of a sensing step two hours after plating. Dendritic cells developed from these lymphocyte-depleted PBMC in the same way as from whole PBMC populations.

Figures 6A, 6B, 6C, 6D:
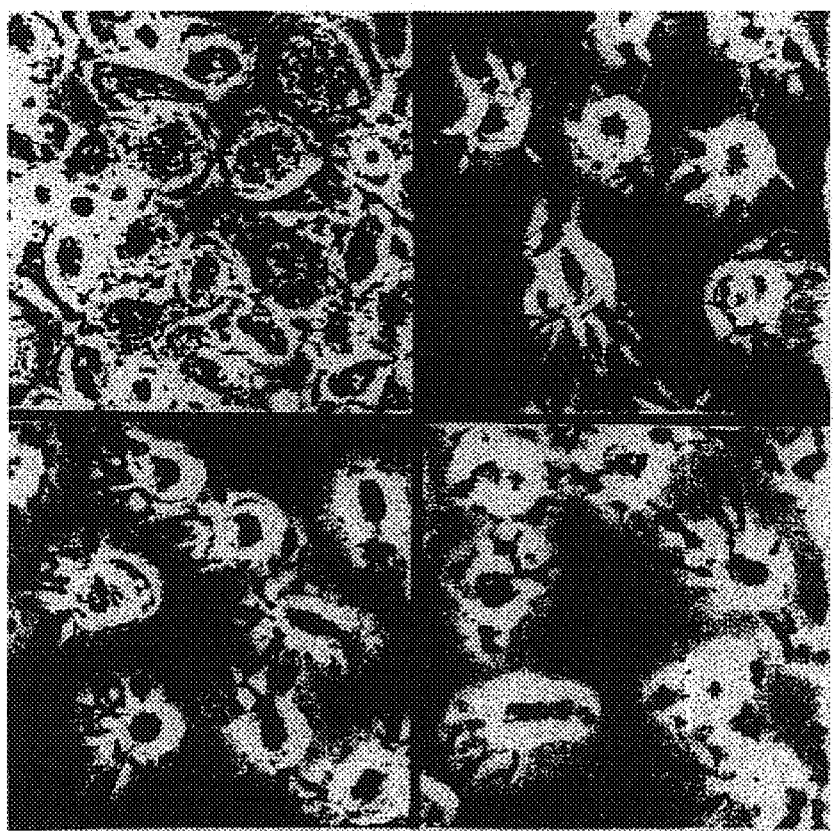
FIG. 6: Morphological stability of mature dendritic cells. Lymphocyte-depleted PBMC were cultured for 10 days in FCS-containing RPMI medium in the presence of GM-CSF and IL-4. Phase contrast micrographs were taken to illustrate the morphology of the cells. [A] No CM was added during the 10 day culture. Cells were washed on day 10 and recultured without cytokines for 3 additional days. They re-adhere firmly and have the appearance of macrophages. [B] CM was added from day 7-10. The cells acquire many lamellipodia or veils and are nonadherent. [C,D] CM was added from day 7-10, the cells were washed and returned to culture for 3 days without CM or cytokines. The morphology of mature dendritic cells persists both in RPMI/10% FCS [C] and X-VIVO 20/serum-free [D] media. A, ×275; B-D, ×550.

Dendritic cells, that had been washed out of GM-CSF and IL-4 and were replated in culture medium without cytokines for an additional three days [days 7-10], lost their characteristic morphology and re-adhered. They assumed the typical shapes of macrophages [FIG. 6A]. In addition, dendritic cells on d7 of culture expressed the macrophage marker CD 115 [c-fms/CSF-1 receptor] although their CD14 expression was very low or absent. In contrast, they did not express CD83, a marker for mature dendritic cells (Zhou and Tedder, 1995) [FIG. 7]. The staining pattern of a well defined population of mature dendritic cells, namely cutaneous dendritic cells obtained by emigration from skin organ cultures (Pope et al. 1995) was inverse: CD115/CD83+ [not shown]. From this we concluded that dendritic cells grown in GM-CSF and IL-4 were not fully and irreversibly mature although they did express some maturation markers such as high levels of MHC class II, furthermore CD40, 54, 58, 80 and a strong T cell stimulatory capacity (Romani et al. 1994; Sallusto and Lanzavecchia, 1994).

Determination of Stimuli for Full Maturation of Dendritic Cells

We tested whether full maturation could be brought about by adding cytokines to the cultures. Supplementation of GM-CSF and IL-4 containing culture medium with IL-1β [50 U/ml] and/or TNF-α [50 U/ml] either from day 0 through to d7 or as a 24-hour pulse from day 0 to day 1 or day 6 to day 7 increased immunostimulatory capacity as expected but did not lead to a stable phenotype of mature dendritic cells as defined above. Addition of these cytokines after the initial 7-day culture and transfer of the cells to fresh culture wells [i.e., from day 7-10] gave the same result [FIG. 8]. Similar findings were made for the cytokines IL-12 [1 ng/ml], stem cell factor/c-kit ligand [yyU/ml] and IL-15 [20 ng/ml].

SACS [fixed *Staphylococcus aureus*], a potent natural stimulator of cytokine secretion was also tested. When a 1:10,000 dilution of SACS was added to the cultures from day 7 to day 10 or 11 of culture, the numbers of free floating dendritic cells increased markedly. Moreover, these cells displayed a more pronounced morphology with highly motile cytoplasmic processes ["veils"]. The cells also did not re-adhere when replated without cytokines. T cell stimulatory capacity in the allogeneic MLR was superior to dendritic cells that had been cultured without SACS [FIG. 8]. However, there was a dramatic stimulation of syngeneic T cells possibly because of superantigens in the SACS preparation. Addition of superantigen to the cultures between days 7 to 10 did not bring about maturation of dendritic cells. However, supernatants of SACS-stimulated adherent PBMC [i.e., conditioned media] had the same effect as SACS itself.

Conditioned medium [CM] was produced in a way that could potentially be of clinical use and avoid the involvement of bacterial products such as SACS. Therefore, we derived supernatants from whole or T-depleted mononuclear cells that had been stimulated by adherence to Ig-coated plates. On day 6 to 8 [mostly 7] of culture dendritic cells were transferred to fresh wells and 25% vol/vol of CM was added. Three to four days later the cells were analyzed. There were almost no adherent cells left on the bottom of the wells. By phase contrast microscopy revealed that the floating cells had many motile veils, much like SACS-treated cells [FIG. 9]. In the hemocytometer the cells appeared "hairy" like cultured epidermal Langerhans cells or cutaneous emigrant dendritic cells. This is in contrast to either 7 day or 10 day cultures without CM, where the cells are large with irregular outlines, but the number of long processes and veils is low. Cultured without cytokines the CM-exposed cells remained stably non-adherent over an observation period of 3 days [FIGS. 6B-D]. They now expressed CD83 and were highly stimulatory for resting T cells [see below]. Therefore, dendritic cells generated in the presence of monocyte CM qualified as fully mature dendritic cells. In >15 experiments the yields of mature, CD83-expressing dendritic cells per 40 ml of blood ranged between 1 and 4×10⁶ in FCS-containing media. Maturation occurred likewise when IL-4 was replaced with IL-13 [20 ng/ml].

To ascertain whether the activity of CM is due to IL-15, a neutralizing antibody was added to CM during the maturation phase of culture. Maturation was not prevented or impaired. We also measured whether CM contained bioactive IL-15. IL-2-responsive CTLL-2 cells also proliferated vigorously in response to both human and simian IL-15 in concentrations as low as 5 pg/ml. No response was seen when CM were tested in this assay [n=2] indicating that IL-15 is present only in minute quantities if at all [Table 8].

TABLE 8

Test for IL-15 in the monocyte conditioned medium

| Additions to the CTLL bioassay for IL-15 | no antibody | anti-IL-5 1:100 | anti-IL-15 1:200 | anti-IL-i5 1:100 + excess IL-15 |
|---|---|---|---|---|
| no cytokines | 0.2 | | | |
| IL-15 [500 pg/ml] | 152.8 | 148.8 | 161.1 | 149.2 |
| IL-15 [50 pg/ml] | 151.1 | 145.3 | 147.0 | 144.2 |
| IL-15 [5 pg/ml] | 45.8 | 0.9 | 0.8 | 156.9 |
| monocyte conditioned medium [25% vol/vol] | 0.6 | 2.4 | 1.1 | 155.0 |

Table 8: IL-15-dependent proliferation of CTLL-2 cells was determined by measuring ³H-TdR incorporation during the final 6 hours of a 36 hour culture [6×10³ CTLL cells per well]. Values are means of triplicate wells and are given in cpm×10⁻³. Excess IL-15 was added at a final concentration of 1 ng/ml.

Development of FCS-Free Media

Having established the conditions for the full maturation of dendritic cells it was desirable to develop a system without fetal calf serum. Simply replacing FCS with human pool sera resulted in little or no development of dendritic cells. We observed increased adherence of cells to the culture surfaces. Serum, plasma and serum from umbilical cord blood were tested over a concentration range from 0.5 to 10%. We also compared autologous sera/plasma versus pooled sera/plasma from the blood bank or commercially available reagents. The effects of heat-inactivation were tested. These variables were combined with different culture media such a RPM1640, X-VIVO, AIM-V, Hybricare, and Iscove's. These reagents were used for the culture of both progenitor cells and CM-producing adherent PBMC. The primary read-out system was morphology under the inverted phase contrast microscope and the yield of mature, stable dendritic cells. Cultures in RPMI supplemented with 10% FCS were always run in parallel as a positive control. RPMI1640 containing 1% autologous, not heat-inactivated human plasma was observed to be optional. In 12 standardized experiments the yield ranged between 0.8 to 3.3×10⁶ CD83+ dendritic cells from 40 ml of blood. Enrichment of CD83+ cells was 30 to 80%.

Properties of Mature Dendritic Cells

Figure 7A:
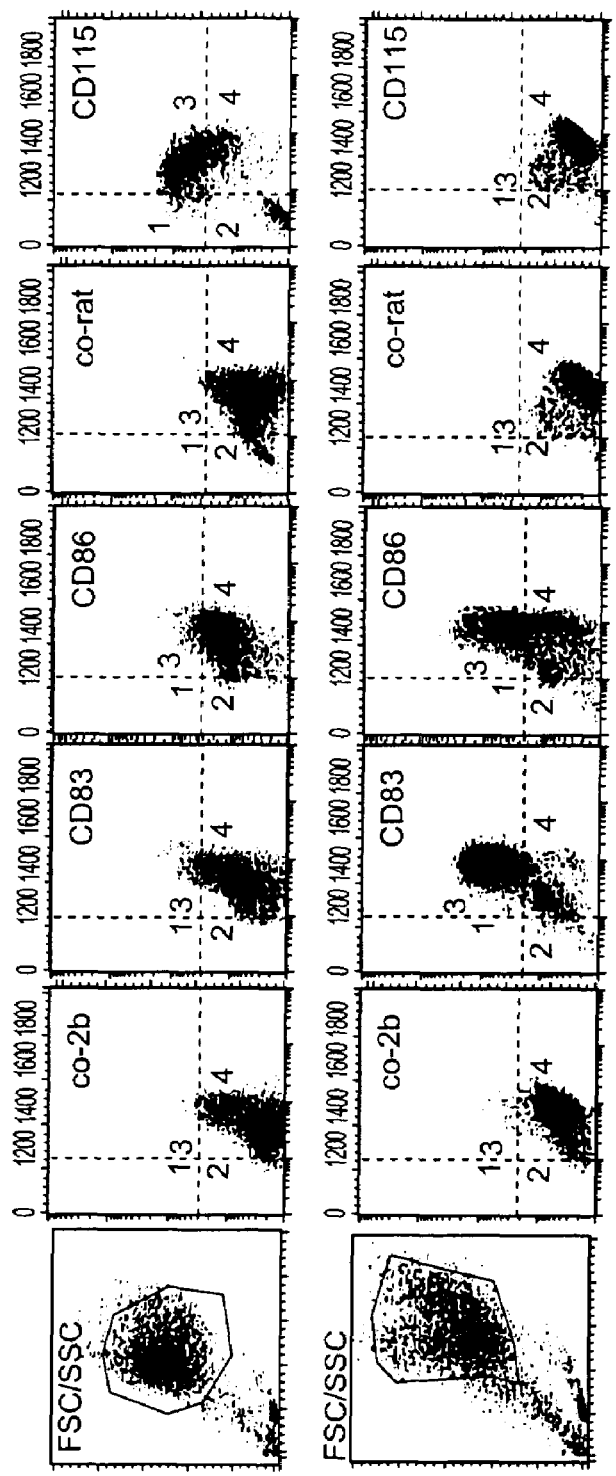
FIG. 7: Comparative cytoflurographic analysis of mature vs. immature dendritic cells. Lymphocyte-depleted PBMC were cultured for 7 days with GM-CSF and IL-4 followed by a maturation period from day 8 to day 10 in the presence of CM. The resulting fully mature dendritic cells were compared to corresponding immature dendritic cells that had not been treated with CM. In all cases mature dendritic cells express CD83 and enhanced levels of CD86, and they lose CD115 expression. [A,A'] Dendritic cells cultured from day 7 to day 10 without [A] or with [A'] CM in RPMI/FCS are shown. Fluorescence on the x-axis represents HLA-DR expression; y-axis shows the indicated antibody staining. Dot plots are from cells gated on the basis of their light scatter properties [FSC/SSC]. [B,B'] Cells were analyzed on day 7[B] and on day 10, i.e., after maturation in the presence of CM [B']. Culture medium was RPMI/1% human plasma; lymphocytes were depleted with immunomagnetic beads. Histograms are from cells gated on the basis of their light scatter properties [FCS/SSC]. [C,C'—left] Like B,B', but lymphocytes were initially depleted by E-rosetting. [C,C'—middle] like B,B', but AIM-V medium/1% human plasma was used. [C,C'—right' like A,A', co-2b, isotype-matched control IgG2b [for CD83, 86, 14]; co-rat, control for rat IgG1 [for CD115]; FSC/SSC, forward scatter/side scatter. All markers are set according to staining with isotype-matched control antibodies.
Figure 7B:
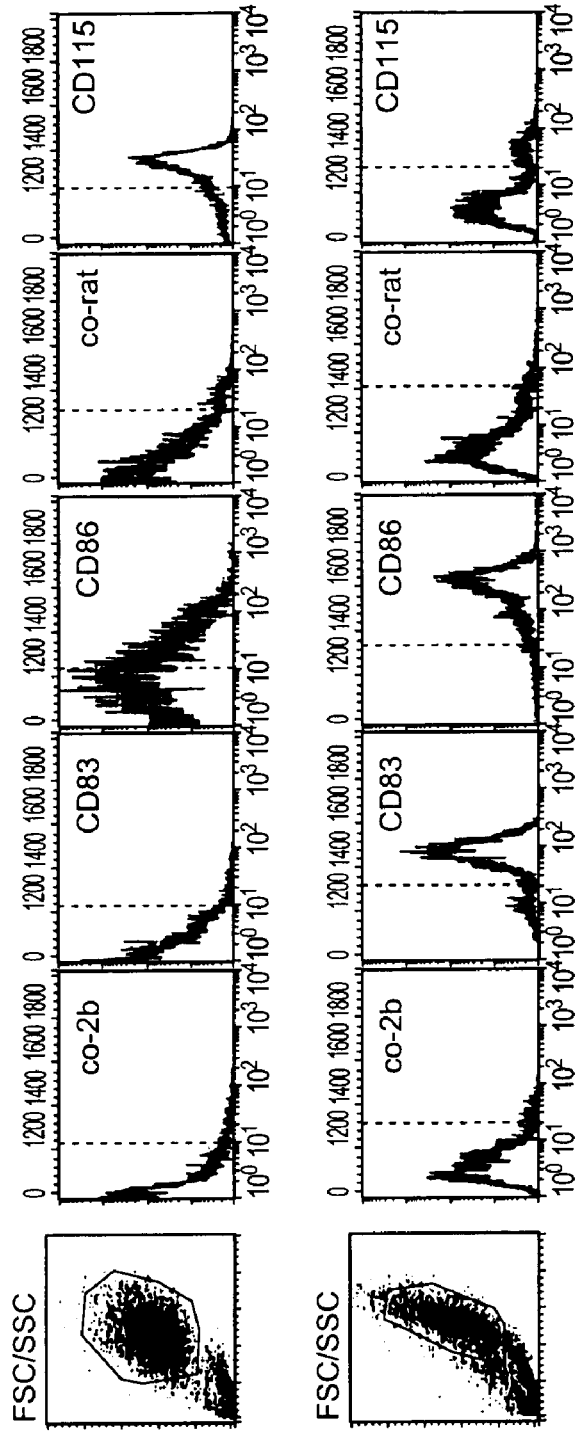
Figure 7C:
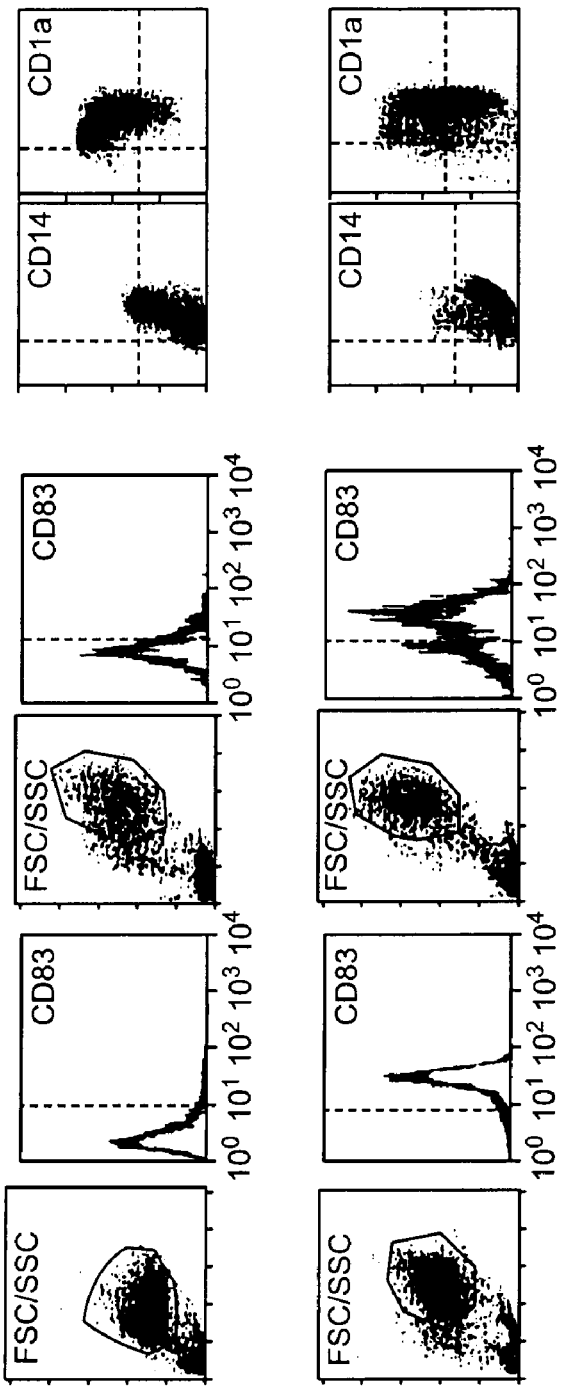

Phenotype. FACS analyses were performed before and three days after exposure to CM. Alternatively, dendritic cells were cultured from day 7 to day 10 in the presence or absence of CM and then compared to each other. FIG. 7 shows expression of the key markers: CD83 is induced, CD86 is enhanced, and CD115 is lost. This pattern applies also to dendritic cells cultured in clinically approved media and derived from PBMC that have been depleted from lymphocytes by immunomagnetic beads or sheep erythrocyte resetting. CD14 is low or absent and CD1a shows some reduction in expression levels upon maturation. Further CM-induced phenotypical changes include the down-regulation of CD32 and CD45RA and the upregulation of CD45RO. Substantial levels of CD4 are expressed on both immature and mature dendritic cells. Staining of cytocentrifuge smears [not shown] also reflected the maturation event that takes place under the influence of CM. Dendritic cells on day 7 of culture are stained throughout the whole cytoplasm in a pattern typical for monocytes or macrophages. After three days of culture in the presence of CM the immunostained cellular structures become concentrated in a dull spot near the nucleus. This pattern has been described for mature dendritic cells. MAb's Lag and Ki-67, specific for Birbeck granules of epidermal dendritic cells [i.e., Langerhans cells] and a proliferation-associated antigen, respectively, stained only rare dendritic cells.

Function. One of the mechanisms by which dendritic cells take up antigens is phagocytosis. This function is down-regulated upon culture of dendritic cells (Reis e Sousa et al. 1993). We tested the phagocytic capacity of dendritic cells before and after exposure to CM. Immature dendritic cells readily took up 2 μm latex beads; mature dendritic cells after three days of culture in CM phagocytosed only very few particles [FIG. 10].

Figure 11D:
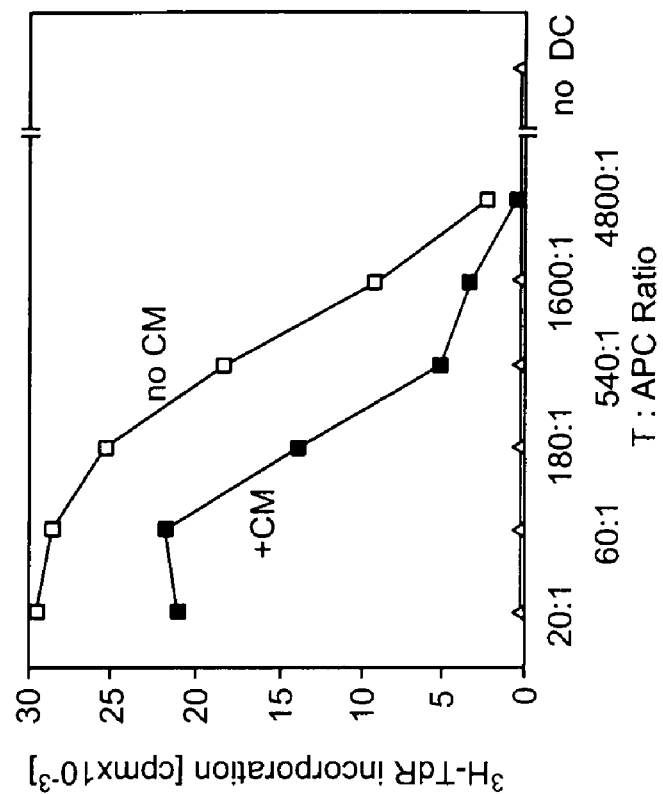
FIG. 11: Immunostimulatory functions of mature dendritic cells. Dendritic cells were cultured in the presence of GM-CSF and IL-4 until day 7 and further on until day 10 with [closed symbols] or without [open symbols] CM. RPMI was supplemented with FCS in A and D-F, and with 1% autologous human plasma in B and C. [A] Note pronounced enhancement of T cell stimulatory capacity in the MLR following exposure to CM. Two independent experiments are shown. [B] Fully mature dendritic cells grown in RPMI supplemented with 10% FCS or 1% autologous human plasma were compared to each other. [C] Fully mature dendritic cells efficiently stimulate naive cord blood T cells. [D]
Figure 11C:
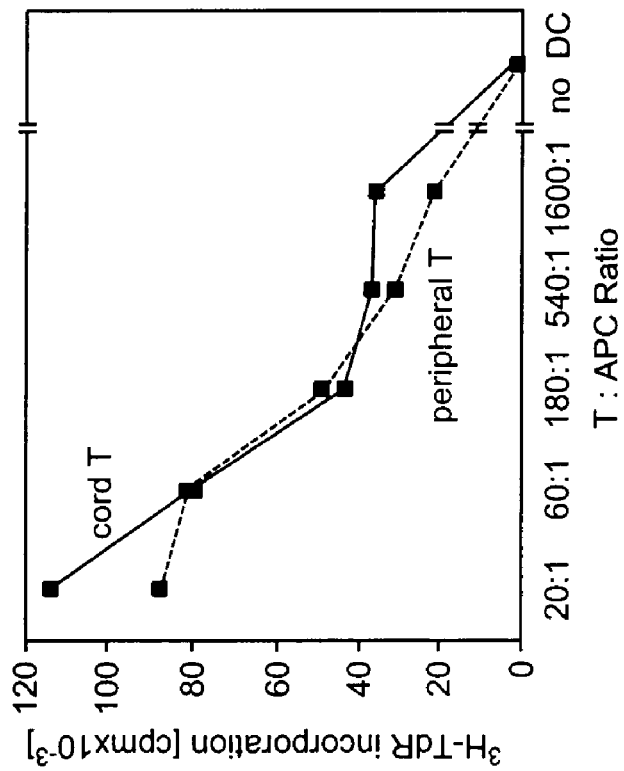
Figures 11E, 11F:
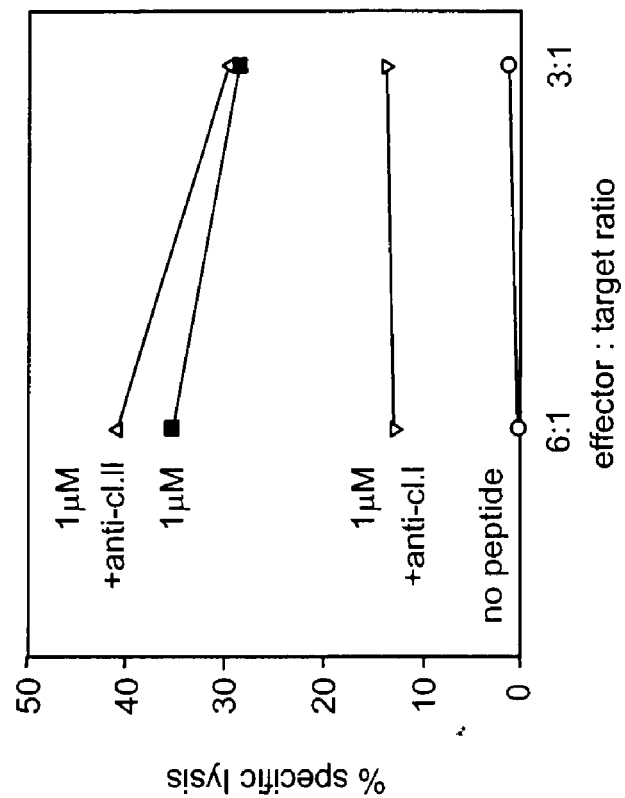

Maturation in conditioned medium enhanced the stimulatory capacity for resting T cells markedly (FIGS. 11A, 11B). Cord T cells, i.e., naive T cells were also efficiently stimulated by mature dendritic cells [FIG. 11C]. When we tested for the capacity to process and present a soluble native protein antigen [tetanus toxoid] using a tetanus peptide-specific T cell clone a reciprocal pattern emerged. Dendritic cells that had been cultured in the presence of CM were less efficient than those cultured in the absence of CM [FIG. 11D] indicating maturation (Sallusto and Lanzavecchia, 1994; Romani et al. 1989a). Mature dendritic cells, when pulsed with a dominant influence matrix peptide that is presented on HLA-A2.1 were able to elicit peptide-specific, MHC class I-restricted, lytic T cells lines from autologous PBMc or populations of CD+ T cells [FIGS. 11E, F].

Modifications of the Method with Regard to Clinical Applicability

With regard to the clinical application of cultured dendritic cells we tested whether the method would work in the complete absence of xenoproteins and with culture media that are approved for clinical use. Comparative data showed that depletion of lymphocytes [T and B] with immunomagnetic beads was equivalent to the commonly used method of resetting with neuramimidase-treated sheep erythrocytes discussed above. Similar numbers of stimulatory dendritic cells were obtained. Anti-B and T cell mouse mAb's and immunomagnetic sheep anti-mouse 1 g beads, both approved for clinical use are available from Baxter Healthcare Corp. [Glendale, Calif.]. Culture media for clinical use are optimized for the growth of cell types other than dendritic cells [e.g. tumor-infiltrating lymphocytes]. Yet, in more than 15 experiments mature dendritic cells could consistently be procured. When X-VIVO 20 medium supplemented with 1% autologous human plasma was used for both culturing the cells and producing CM, substantial numbers of stimulatory dendritic cells could be obtained. Yields and percentages of enrichment were, however, only about half of what could be achieved with RPMI 1640 medium [n=5]. More adherent cells were observed in these cultures. Pilot experiments with AIM-V medium gave similar results. X-VIVO 10 and X-VIVO 15 media yielded unsatisfactory results.

With regard to the possibility that only small volumes of blood may be available in certain clinical settings we determined that pretreatment of donors with G-CSF increased dendritic cell yields. Blood from G-CSF-treated cancer patients and normal individuals gave up to 6-fold yields of mature [i.e., CD83+] dendritic cells. This increase was not only due to an increased frequency of CD34+ precursor cells in the blood because similar numbers of immunostimulatory mature dendritic cells could be grown both from CD34-containing and CD34-depleted PBMC starting populations in response to GM-CSF, IL-4 and CM [FIG. 12].

We also tested whether cryopreservation of dendritic cells precursors and their progeny is possible. Indeed, using standard freezing procedures dendritic cells could be generated from thawed populations of PBMC. Although not investigated systematically, it is preferred to freeze the starting population of PBMC or immature dendritic cells on day 7 of culture [i.e.], the day of transfer into CM-containing medium rather than mature cells on day 10/11 of culture.

The criteria used initially to define fully mature dendritic cells included: morphology, lack of adherence to plastic, and select surface markers. Dendritic cells grown for six days in GM-CSF and IL-4, i.e., immature dendritic cells did not express CD83 but did express CD115 [CSF-1 receptor/M-CSF receptor]. When they were replated without cytokines [and without CM] they adhered to the bottom of the culture wells. After a three day culture in the presence of CM they became CD83+/CD115- and did not become adherent upon withdrawal of cytokines. They also maintained their pronounced cytoplasmic, motile "veils". These results are consistent with the production of fully and stably mature dendritic cells. Only SACS, conditioned media from SACS-stimulated adherent PBMC, and conditioned media from monocytes stimulated by adherence on Ig were able to make dendritic cells reach full maturation. When we tried to replace CM with cytokines we observed no effects or some increase in T cell stimulatory capacity [with IL-1β, and/or TNF-α or IL-15]. Full maturation was not achieved, however. In as shown in Example 1, neutralizing antibodies to IL-1α and β, IL-6, TNF-α, IL-12, alone or in combination, do not block the activity of the monocyte CM. CM may contain either a unique cocktail of cytokines that is difficult or impossible to reproduce experimentally or new cytokines.

Example 3

Clinical Use of Dendritic Cells Primed with Influenza or HIV Antigens

In this Example, dendritic cells prepared as described in Example 1 are primed with peptides that are presented on MHC class I molecules to prime CD8+ T cells. We have used the immunodominant influenza matrix peptide, GILGFVFTL (SEQ ID NO:1), that is recognized by CTLs from HLA-2.1 individuals, and we will in addition use HIV-1 peptides [pol ILKEPVHOV (SEQ ID NO:2); gag SLYNTVATL (SEQ ID NO:3)] that are recognized by CTLs from HIV-1 infected individuals. The efficacy of the peptide pulse can be monitored by applying an aliquot of the DCs to autologous T cells in culture and measuring the killer cell response.

Most humans are primed to influenza antigens, so that the recall CTL response to this virus provides an optimal and internal control to determine if autologous DCs, pulsed ex vivo with viral antigens, can boost the CTL response in vivo.

In this protocol, HIV-1 infected individuals are treated with CD4+ T cell counts of 300-400/ul. These individuals have low numbers of HIV-1 specific, killer cell precursors. Asymptomatic, HIV-1 infected, adult volunteers of both sexes will be recruited. The donors must be HLA-A2.1 positive, as will be determined by initial typing with a monoclonal to A2.1. Donors who have relatively low and high recall responses to influenza will be included. The therapeutic goal is to increase the numbers of these killers in order to reduce the cell-cell spread of HIV-1. The killer cell response to influenza is an internal control, since it should be intact in HIV-1 infected patients.

Pairs of HIV-1 peptides are used so that the response to dendritic cells administered by two routes, intradermal [i.d.] and subcutaneous [s.c.] can be compared in the same patient. The influenza peptide will serve as the common denominator for each route. The peptides are made according to Good Laboratory Practices [GLP] at Sloan Kettering Institute, where peptides have been synthesized previously for administration in humans.

The Clinical Protocol is as Follows:

a. Take a 50-60 ml blood sample in heparin by venipuncture.

b. Isolate the mononuclear cells on Ficoll Hypaque, and save the autologous plasma.

c. Separate the mononuclear cells into T cell enriched and T cell depleted fractions by sheep erythrocyte resetting, or by depleting lymphocytes with GMP-grade DYNAL beads coated with monoclonal antibodies to B and T cells. The T cells are frozen for tissue culture tests for antigen presentation to cytolytic T lymphocytes [CTLs, below].

d. Culture a fraction of the mononuclear cells on culture plates that have been coated with human Ig [Sandoz] in an RPMI-1640 culture medium supplemented with antibiotics [penicillin and streptomycin]. This stimulates the cells to form a conditioned medium that fosters DC maturation.

e. Culture the bulk of the T-depleted mononuclear cells for 6 days in RPMI-1640 supplemented with antibiotics, 1% autologous plasma, 1000 U/ml rHuGM-CSF, and 1000 U/ml rHuIL-4. GMP grade cytokines are provided by Schering-Plough.

f. After 6 days, transfer the cells to fresh medium supplemented with 30-50% v/v autologous monocyte conditioned medium plus 1 uM of influenza matrix peptide, GILGFVFTL (SEQ ID NO:1). One aliquot of the DCs is pulsed with the HIV-1 gag peptide (SEQ ID NO:3) and the other with the polymerase peptide (SEQ ID NO:2). At day 11, when the DCs have acquired their typical stellate shapes, the DCs are harvested, washed, counted, and readied for injection by s.c, and i.d. routes. Prior to the injection, the patients are typed to be sure that they have killed cell precursors specific for the above peptides.

g. The DCs are injected in the forearm. On one side the cells are given in a total of 0.5 ml in 3 intradermal sites, while on the other side, the cells are given in 0.5 ml in 3 subcutaneous sites. The purpose of the two routes is to compare the efficacy of boosting to the influenza matrix peptide.

h. 1 week and 1 month after injection, 25 ml of blood is taken to evaluate the induction of immune responses. T cell responsiveness to the peptide is measured by antigen-induced proliferation and release of IFN-gamma in culture. The results are compared to preinjection values which are obtained 0 and 1 month prior to injection. The first injection utilizes DCs that are not pulsed with peptide. T cell responsiveness to peptide will be measured by enumerating CTL precursor frequencies [CTLp] for the peptide-coated, HLA-A2.1 "T2" cell line.

i. If priming is not detected at 1 month, a second dose of antigen pulsed DCs is be administered. If priming is detected at 1 month, the immune status is reexamined at 3 months and 6 months to determine the longevity of immune memory.

While we have hereinbefore described a number of embodiments of this invention, it is apparent that the basic constructions can be altered to provide other embodiments which utilize the methods and compositions of the invention. Therefore, it will be appreciated that the scope of this invention is defined by the claims appended hereto rather than by the specific embodiments which have presented hereinbefore by way of example.

BIBLIOGRAPHY

Alijagic, S., Moller, P., Artuc, M., Jorgovsky, K., Czarnetzki, B. M. and Schadendorf, D. (1995). Dendritic cells generated from peripheral blood transfected with human tyrosinase induce specific T cell activation. Eur. J. Immunol. 25, 3100.

Ashuman, R. A., Look, A. T., Roberts, W. M., roussel, M. F., Seremetis, S., Ohtsuka, M., and Sherr, C. J. (1989). Monoclonal antibodies to the human CSF-1 receptor (c-fms protooncogene product) detect epitopes on normal mononuclear phagocytes and on human myeloid leukemic blasts. Blood 73, 827-837.

Austyn, J. M. (1987) Lymphoid dendritic cells. Immunol. 62, 161.

Bakker, A. B. H., Marland, G., De Boer, A. J., Huijbens, R. J. F., Danen, E. H. J., Adema, G. J. and Figdor, C. G. (1995) Generation of antimelanoma cytotoxic T lymphocytes from healthy donors after presentation of melanoma-associated antigen-derived eptiopes by dendritic cells in vitro. Cancer Res. 55, 5330.

Bender, A., Bui, L. K., Feldman, M. A. V., Larsson, M. and Bhardwaj, N. (1995) Inactivated influenza virus, when presented on dendritic cells, elicits human CD8$^+$ cytolytic T cell responses. J. Exp. Med. 182, 1663.

Bhardwaj, N., Lau, L., Rivelis, M. and Steinman, R. M. (1988) Interleukin-1 production by mononuclear cells from rheumatoid synovial effusions. Cell. Immunol. 114, 405.

Bhardwaj, N., Bender, A., Gonzalez, N., Bui, L. K., Garrett, M. C. and Steinman, R. M. (1994) Influenza virus-infected dendritic cells stimulate strong proliferative and cytolytic responses from human CD8+ T cells. J. Clin. Invest. 94, 797.

Boon, T., Cerottini, J.-C., Van den Eynde, B., Van der Bruggen, P. and Van Pel, A. (1994). tumor antigens recognized by T lymphocytes. Annu. Rev. Immunol. 12, 337.

Carr, C. M. and Kim, P. S. (1993) A spring-loaded mechanism for the conformational change of influenza hemagglutinin. Cell 73, 823.

Caux, C., Dezutter-Dambuyant, C., Schmitt, D. and Bancherau, J. (1992) GM-CSF and TNF-alpha cooperate in the generation of dendritic Langerhans cells. Nature 360, 258.

Caux, C., Massacrier, C., Vanbervliet, B., Dubois, B., Van Kooten, C., Durand, I. and Banchereau, J. (1994) Activation of human dendritic cells through CD40 cross-linking. J. Exp. Med. 180, 1263.

Caux, C., Liu, Y.-J. and Banchereau, J. (1995a) Recent advances in the study of dendritic cells and follicular dendritic cells. Immunol. Today 16, 2.

Caux, C., Massacrier, C., Dezutter-Dambuyant, C., Vanbervliet, B., Jacquet, C., Schmitt, D. and Banchereau, J. (1995b) Human dendritic Langerhans cells generated in vitro from CD34$^+$ progenitors can prime naive CD4$^+$ T cells and process soluble antigen. J. Immunol. 155, 5427.

Crowley, M., Inaba, K. and Steinman, R. M. (1990) Dendritic cells are the principal cells in mouse spleen bearing immunogenic fragments of foreign proteins. J. Exp. Med. 172, 383.

De Bruijin, M. L. H., Nieland, J. D., Schumacher, T. N. M., Ploegh, H. L., Kast, W. M. and Melief, C. J. M. (1992) Mechanisms of induction of primary virus-specific cytotoxic T lymphocyte responses. Eur. J. Immunol. 22, 3013.

Egner, W. and Hart, D. N. J. (1995). The phenotype of freshly isolated and cultured human bone marrow allositmulatory cells: Possible heterogeneity in bone marrow dendritic cell populations. Immunology 85, 611.

Fossum, S. (1989a) Lymph-borne dendritic leucocytes do not recirculate, but enter the lymph node paracortex to become interdigitating cells. Scand. J. Immunol. 27, 97.

Fossum, S. (1989b) The life history of dendritic leukocytes [DL]. In: O. H. Ivessen (Ed.), Current Topics in Pathology. Springer-Verlag, Berlin, p. 101.

Hart, D. N. J. and McKenzie, J. L. (1990) Interstitial dendritic cells. Intl. Rev. Immunol. 6, 128.

Helfgott, D. C., Tatter, S. B., Santhanam, U., Clarick, R. H., Bhardwaj, N., May, L. T. and Sehgal, P. B. (1988) Interferon-beta 2/intereleukin-6 in plasma and body fluids during acute bacterial infection. J. Immunol. 142, 948.

Inaba, K., Metlay, J. P., Crowley, M. T. and Steinman, R. M. (1990a) Dendritic cells pulsed with protein antigens in vitro can prime antigen-specific, MHC-restricted T cells in situ. J. Exp. Med. 172, 631.

Inaba, K., Metlay, J. P., Crowley, M. T., Witmer-Pack, M. and Steinman, R. M. (1990b) Dendritic cells as antigen presenting cells in vivo. Intl. Rev. Immunol. 6, 197.

Inaba, K., Steinman, R. M., Witmer-Pack, M., Aya, K., Inaba, M., Sudo, T., Wolpe, S. and Schuler, G. (1992) Identification of Proliferating Dendritic Cell Precursors In Mouse Blood. J. Exp. Med., 175:1157.

Jonuliet, H., Kohn, U., Muller, G., Wolfl, M., Lohmann, S., Saloga, J., Becker, D., Knop, J., and A. H. Enk, A. H.) 1995). Keratinocyte-derived IL-15 enhances accessory functions of epidermal Langerhans cells and blood dendritic cells. J. Invest. Dermatol. 105, 861 [abstract].

Kashithara, M., Ueda, M., Horiguchi, Y., Furukawa, F., Hanaoka, M. and Imamura, S. (1986). A monoclonal antibody specifically reactive to human Langerhans cells. J. Invest. Dermatol. 87, 602.

Klareskog, L., Ronnelid, J. and Holm, G. (1995) Immunopathogenesis and immunotherapy in rheumatoid arthritis: an area in transition. J. Int. Med. 238, 191.

Lanzavecchia, A. (1985). Antigen-specific interaction between T and B cells. Nature 314, 537.

Larsen, C. P., Ritchie, S. C., Hendrix, R., Linsley, P. S., Hathcock, K. S., Hodes, R. J., Lowry, R. P. and Pearson, T. C. (1994). Regulation of immunostimulatory function and costimulatory molecule (B7-1 and B7-2) expression on murine dendritic cells. J. Immunol. 152, 5208.

Lenz, A., Heine, M., Schuler, G. and Romani, N. (1993). Human and murine dermis contain dendritic cells. J. Clin. Invest. 92, 2587.

Mason, D. W., Pugh, C. W. and Webb, M. (1981) The rat mixed lymphocyte reaction: roles of a dendritic cell in intestinal lymph and T cell subsets defined by monoclonal antibodies. Immunol. 44, 75.

Mayordomo, J. I., Zorina, T., Storkus, W. J., Zitvogel, L., Celluzzi, C., Falo, L. D., Melief, C. J., Ilstad, S. T., Kast, W. M., DeLeo, A. B. and Lotze, M. T. (1995) Bone marrow-derived dendritic cells pulsed with synthetic tumour peptides elicit protective and therapeutic antitumor immunity. Nature Med. 1, 1297.

McWilliam, A. S., Nelson, D., Thomas, J. A. and Holt, P. G. (1994) Rapid dendritic cell recruitment is a hallmark of the acute inflammatory response at mucosal surfaces. J. Exp. Med. 179, 1331.

Mosialos, G., Birkenbach, M., Ayehunie, S., Matsumura, F., Pinkus, G. S., Kieff, E. and Langhoff, E. (1996) Circulating human dendritic cells differentially express high levels of a 55-KD actin bundling protein. Am. J. Pathol. In Press.

O'Doherty, U., Steinman, R. M., Peng, M., Cameron, P. U., Gezelter, S., Kopeloff, I., Swiggard, W. J., Pope, M. and Bhardwaj, N. (1993) Dendritic cells freshly isolated from human blood express CD4 and mature into typical immunostimulatory dendritic cells after culture in monocyte-conditioned medium. J. Exp. Med. 178, 1067.

O'Doherty, U., Peng, M., Gezelter, S., Swiggard, W. J., Betjes, M., Bhardwaj, N. and Steinman, R. M. (1994) Human blood contains two subsets of dendritic cells, one immunologically mature, and the other immature. Immunol. 82, 487.

Pope, M., Betjes, M. G. H., Hirmand, H., Hoffman, L. and Steinman, R. M. (1995) Both dendritic cells and memory T lymphocytes emigrate from organ cultures of human skin and form distinctive dendritic T-cell conjugates. J. Invest. Dermatol. 104, 11.

Porgador, A. and Gilboa, E. (1995) Bone marrow-generated dendritic cells pulsed with a class I-restricted peptide are potent inducers of cytotoxic T lymphocytes. J. Exp. Med. 182, 255.

Pugh, C. W., MacPherson, G. G. and Steer, H. W. (1983) Characterization of nonlymphoid cells derived from rat peripheral lymph. J. Exp. Med. 157, 1758.

Rabinowitz, S. S. and Gordon, S. (1991) Macrosialin, a macrophage-restricted membrane sialoprotein differentially glycosylated in response to inflammatory stimuli. J. Exp. Med. 174, 827.

Ramprasad, M. P., Fischer, W., Witztum, J. L., Sambrano, G. R., Quehenberger, O. and Steinberg, D. (1995) The 94- to 97-kDa mouse macrophage membrane protein that recognizes oxidized low density lipoprotein and phosphatidylserine-rich liposomes is identical to macrosialin, the mouse homologue of human CD68. Proc. Natl. Acad. Sci. USA 92, 9580.

Reid, C. D. L., Stackpoole, A. Meager, A. and Tikerpae, J. (1992) Interactions of tumor necrosis factor with granulocyte-macrophage colony stimulating factor and other cytokines in the regulation of dendritic cell growth in vitro from early biopotent CD34$^+$ progenitors in human bone marrow. J. Immunol. 149, 509.

Reis e Sousa, C., Stahl, P. D. and Austyn, J. M. (1993) Phagocytosis of antigens by Langerhans cells in vitro. J. Exp. Med. 178, 509.

Romani, N., Gruner, S., Brang, D., Kampgen, E., Lenz, A., Trockenbacher, B., Konwalinka, G., Fritsch, P. O., Steinman, R. M. and Schuler, G. (1994) Proliferating dendritic cell progenitors in human blood. J. Exp. Med. 180, 83.

Romani N., Koide, S., Crowley, M., Witmer-Pack, M., Livingstone, A. M., Fathman, C. G., Inaba, K. and Steinman, R. M. (1989a) Presentation of exogenous protein antigens by dendritic cells to T cell clones: intact protein is presented best by immature epidermal Langerhans cells. J. Exp. Med. 169, 1169.

Romani, N., Lenz, A., Glassel, H., Stossel, H., Stanzi, U., Majdic, 0., Fritsch, P. and Schuler, G. (1989b) Cultured human Langerhans cells resemble lymphoid dendritic cells in phenotype and function. J. Invest. Dermatol. 93, 600.

Sallusto, F., Cella, M., Danieli, C. and Lanzavecchia, A. (1995) Dendritic cells use macropinocytosis and the mannose receptor to concentrate macromolecules in the major histocompatibility complex class II compartment: Downregulation by cytokines and bacterial products. J. Exp. Med. 182, 389.

Sallusto, F. and Lanzavecchia, A. (1994) Efficient presentation of soluble antigen by cultured human dendritic cells is maintained by granulocyte/macrophage colony-stimulating factor plus interleukin 4 and downregulated by tumor necrosis factor α. J. Exp. Med. 179, 1109.

Sallusto, F. and Lanzavecchia, A. (1995) Dendritic cells use macropinocytosis and the mannose receptor to concentrate antigen in the MHC class II compartment. Downregulation by cytokines and bacterial products. J. Exp. Med. 182, 389.

Schuler, G. and Steinman, R. M. (1985) Murine epidermal Langerhans cells mature into potent immunostimulatory dendritic cells in vitro. J. Exp. Med. 161, 526.

Steinman, R. M. (1991) The dendritic cell system and its role in immunogenicity. Annu. Rev. Immunol. 9, 271.

Steinman, R. M., Hoffman, L. and Pope, M. (1995) Maturation and migration of cutaneous dendritic cells. J. Invest. Dermatol. 105 2S.

Teunissen, M. B. M., Wormmeester, J., Krieg, S. R., Peters, P. J., Vogels, I. M. C., Kapsenberg, M. L., and Bos, J. D. (1990) Human epidermal Langerhans cells undergo profound morphological and phenotypical changes during in vitro culture. J. Invest. Dermatol. 94, 166.

Thomas, R., Davis, L. S. and Lipsky, P. E. (1993) Isolation and characterization of human peripheral blood dendritic cells. J. Immunol. 150, 821.

Thomas, R., Davis, L. S. and Lipsky, P. E. (1994) Rheumatoid synovium is enriched in mature antigen-presenting dendritic cells. J. Immunol. 152, 2613.

Watson, S. R., Imai, Y., Fennie, C., Geoffroy, J. S., Rosen, S. D. and Lasky, L. A. (1990) A homing receptor-IgG chimera as a probe for adhesive ligands of lymph node high endothelial venules. J. Cell Biol. 110, 2221.

Young, J. W. and Steinman, R. M. (1988) Accessory cell requirements for the mixed-leukocyte reaction and polyclonal mitogens, as studied with a new technique for enriching blood dendritic cells. Cell. Immunol. 111, 167.

Young, J. W. and Steinman, R. M. (1990) Dendritic cells stimulate primary human cytolytic lymphocyte responses in the absence of CD4[+] helper T cells. J. Exp. Med. 171, 1315.

Zhou, L.-J., Schwarting, R., Smith, H. M. and Tedder, T. F. (1992) A novel cell-surface molecule expressed by human interdigitating reticulum cells, langerhans cells, and activated lymphocytes is a new member of the Ig superfamily. J. Immunol. 149, 735.

Zhou, L.-J. and Tedder, T. F. (1995) Human blood dendritic cells selectively express CD83, a member of the immunoglobulin superfamily. J. Immunol. 154, 3821.

Zitvogel, L., Mayordomo, J. I., Tjandrawan, T., DeLeo, A. B., Clarke, M. R., Lotze, M. T. and Storkus, W. J. (1996) Therapy of murine tumors with tumor peptide pulsed dendritic cells: Dependence on T-cells, B7 costimulation, and Th1-associated cytokines. J. Exp. Med. In press.

Zvaifler, N. J., Steinman, R. M., Kaplan, G., Lau, L. L. and Rivelis, M. (1985) Identification of immunostimulatory dendritic cells in the synovial effusions of patients with rheumatoid arthritis. J. Clin. Invest. 76, 789.

All of the foregoing are incorporated herein by reference.

We claim:

1. An in vitro method of producing stable mature CD83 positive dendritic cells from substantially CD83 negative immature dendritic cells which are derived from PBMC pluripotential cells having the potential of expressing either macrophage or dendritic cell characteristics, said method comprising the steps of:
   (a) culturing a population of peripheral blood mononuclear cells comprising pluripotential cells which are CD14 positive and substantially CD83 negative with at least one cytokine to produce a population of immature dendritic cells characterized as substantially CD14 and CD83 negative; and
   (b) culturing said substantially CD83 negative immature dendritic cells in the presence of a composition selected from the group consisting of fixed *Staphylococcus aureus* (SACS), peripheral blood mononuclear cell conditioned medium, and monocyte conditioned medium, in an amount and for a time sufficient for said immature dendritic cells to express characteristics of mature dendritic cells, wherein said characteristics of mature dendritic cells include an increase in CD83 and CD11c expression, a decrease in CD68 expression, and persistence of non-adherence for three days following removal of said composition from said culture of dendritic cells.

2. The method according to claim 1, wherein the composition is monocyte conditioned medium.

3. The method according to claim 1, wherein the cytokine is a combination of GM-CSF and either one or both of IL-4 and IL-13.

4. The method according to claim 3, wherein said pluripotential cells are human.

5. The method according to claim 4, wherein said pluripotential cells are obtained from human blood.

6. The method according to claim 5, wherein the cytokine is a combination of GM-CSF and IL-4.

7. The method of claim 1, wherein said composition is peripheral blood mononuclear cell conditioned medium.

8. The method of claim 1, wherein said composition is macrophage conditioned medium.

9. The method of claim 1, wherein said composition is fixed *Staphylococcus aureus* (SACS).

10. The method of claim 1, wherein said immature dendritic cells are obtained by culturing a population of peripheral blood mononuclear cells with at least one cytokine in medium which does not contain fetal calf serum.

* * * * *

SEQUENCE LISTING

```
<160> NUMBER OF SEQ ID NOS: 3

<210> SEQ ID NO 1
<211> LENGTH: 9
<212> TYPE: PRT
<213> ORGANISM: Influenza matrix peptide

<400> SEQUENCE: 1

Gly Ile Leu Gly Phe Val Phe Thr Leu
1               5

<210> SEQ ID NO 2
<211> LENGTH: 9
<212> TYPE: PRT
<213> ORGANISM: Human Immunodeficiency Virus Type 1

<400> SEQUENCE: 2

Ile Leu Lys Glu Pro Val His Gly Val
1               5

<210> SEQ ID NO 3
<211> LENGTH: 9
<212> TYPE: PRT
<213> ORGANISM: Human Immunodeficiency Virus Type 1

<400> SEQUENCE: 3

Ser Leu Tyr Asn Thr Val Ala Thr Leu
1               5
```